(12) United States Patent
Lucas et al.

(10) Patent No.: US 7,259,011 B2
(45) Date of Patent: Aug. 21, 2007

(54) PLURIPOTENT ADULT STEM CELLS

(76) Inventors: Paul Lucas, 36 Carol Dr., Poughkeepsie, NY (US) 12603; Sherri Schultz, 30 Cortlandt Manor Rd., Katonah, NY (US) 10536; Sharon P. Pine, 19395 Keymar Way, Montgomery Village, MD (US) 20886

( * ) Notice: Subject to any disclaimer, the term of this patent is extended or adjusted under 35 U.S.C. 154(b) by 92 days.

(21) Appl. No.: 11/133,596

(22) Filed: May 20, 2005

(65) Prior Publication Data
US 2005/0260751 A1 Nov. 24, 2005

Related U.S. Application Data

(60) Provisional application No. 60/572,494, filed on May 20, 2004.

(51) Int. Cl.
*C12N 5/00* (2006.01)
*C12N 5/08* (2006.01)
*C12N 5/02* (2006.01)

(52) U.S. Cl. ................. 435/366; 435/372; 435/395

(58) Field of Classification Search ............... 424/93.1; 435/366
See application file for complete search history.

(56) References Cited

U.S. PATENT DOCUMENTS

| | | | |
|---|---|---|---|
| 5,328,695 A | 7/1994 | Lucas et al. | 424/426 |
| 5,486,359 A | 1/1996 | Caplan et al. | 424/93.7 |
| 5,827,735 A | 10/1998 | Young et al. | 435/325 |
| 5,906,934 A | 5/1999 | Grande et al. | 435/325 |
| 6,214,369 B1 | 4/2001 | Grande et al. | 424/423 |
| 2003/0040023 A1 | 2/2003 | Klassen et al. | 435/721 |
| 2003/0064503 A1 | 4/2003 | Abuljadayel | 435/285.1 |
| 2003/0161817 A1 | 8/2003 | Young et al. | 424/93.21 |
| 2004/0033214 A1 | 2/2004 | Young et al. | 424/93.7 |

OTHER PUBLICATIONS

Shieh et al. State-of-the-art tissue engineering: From tissue engineering to organ building. Surgery (Jan. 2005) vol. 137(1), pp. 1-7.*
Dawson et al. Safety issues in cell-based intervention trials. Fertility and Sterility (2003) vol. 80(5), pp. 1077-1085.*
LeRou et al. Therapeutic potential of embryonic stem cells. Blood Reviews (2005), pp. 1-11.*
Nagy et al. Stem cell transplantation as therapeutic approach to organ failure. Journal of Surgical Research (available online Sep. 27, 2005), pp. 1-9.*
Arriero et al. Adult skeletal muscle stem cells differentiate into endothelial lineage and ameliorate renal dysfunction after acute ischemia. Am J Physiol Renal Physiol. Oct. 2004; 287(4):F621-7.
Jiang et al. Multipotent progenitor cells can be isolated from postnatal murine bone marrow, muscle, and brain. Exp Hematology 2002; 30:896-904.
Jiang et al. Pluripotency of mesenchymal stem cells derived from adult marrow. Nature advance online publication, Jun. 2002 (doi:10.1038/nature00870).
Lucas et al. A population of cells resident within embryonic and newborn rat skeletal muscle is capable of differentiating into multiple mesodermal phenotypes. Wound Repair Regeneration 1995; 3:449-60.
Prockop. Marrow stromal cells as stem cells for nonhematopoietic tissues. Science Apr. 1997; 276: 71-4.
Qu-Petersen et al. Identification of a novel population of muscle stem cells in mice: potential for muscle regeneration. Jour of Cell Bio May 2002; 157(5): 851-64.
Rogers et al. Differentiation factors induce expression of muscle, fat, cartilage, and bone in a clone of mouse pluripotent mesenchymal stem cells. Am Surg. Mar. 1995; 61(3):231-6.
Romero-Ramos et al. Neuronal differentiation of stem cells isolated from adult muscle. Jour of Neurosci Res 2002; 69: 894-907.
Toma et al. Isolation of multipotent adult stem cells from the dermis of mammalian skin. Nature Cell Biol Sep. 2001; 3:778-84.
Tuckman et al. The use of mesenchymal stem cells for the repair of meniscal defects in rabbits. Transactions of the 48th Annual Meeting, Orthopedic Research Society, 2002, abstract.
Vourc'h et al. Isolation and characterization of cells with neurogenic potential from adult skeletal muscle. Biochem Biophys Res Commun. May 7, 2004; 317(3) 893-901.
Warejcka et al. A population of cells isolated from rat heart capable of differentiating into several mesodermal phenotypes. J Surg. Res. May 1996; 62(2) 233-42.
Woodbury et al. Adult bone marrow stromal stem cells express germline, ectodermal, endodermal, and mesodermal genes prior to neurogenesis. Jour of Neurosci 2002; 69(6): 908-17.
Woodbury et al. Adult rat and human bone marrow stromal cells differentiate into neurons. Jour of Neurosci Res 2000; 61:364-70.
Young et al. Bioactive factors affect proliferation and phenotypic expression in progenitor and pluripotent stem cells. Wound Repair Regen. Jan.-Feb. 1998; 6(1):66-75.
Young et al. Human pluripotent and progenitor cells display cell surface cluster differentiation markers CD10, CD13, CD56, and MHC class-1. Proc Soc Exp Biol Med. May 1999; 221(1):63-71.
Young et al. Human reserve pluripotent mesenchymal stem cells are present in the connective tissues of skeletal muscle and dermis derived from fetal, adult, and geriatric donors. The Anatomical Record 2001; 264:51-62.
Young et al. Mesenchymal stem cells reside within the connective tissues of many organs. Sev. Dyn. Feb. 1995; 202(2): 137-44.
Young et al. Pluripotent mesenchymal stem cells reside within avian connective tissue matrices. In Vitro Cell Dev Biol Anim. Sep. 1993; 29A(9):723-36.
Zeman et al. Pluripotent stem cell implantation in spinal cord injury. United Spinal Association, Las Vegas, Sep. 12-14, 2003, abstract.

* cited by examiner

*Primary Examiner*—Celine Qian
*Assistant Examiner*—Laura McGillem
(74) *Attorney, Agent, or Firm*—Nada Jain, P.C.

(57) ABSTRACT

The invention relates to isolated human pluripotent adult stem cells which express CD13, CD34, CD56 and CD117, and which do not express CD1O, which are capable of differentiating in all three germ lineages and differentiated cells derived therefrom.

15 Claims, 16 Drawing Sheets

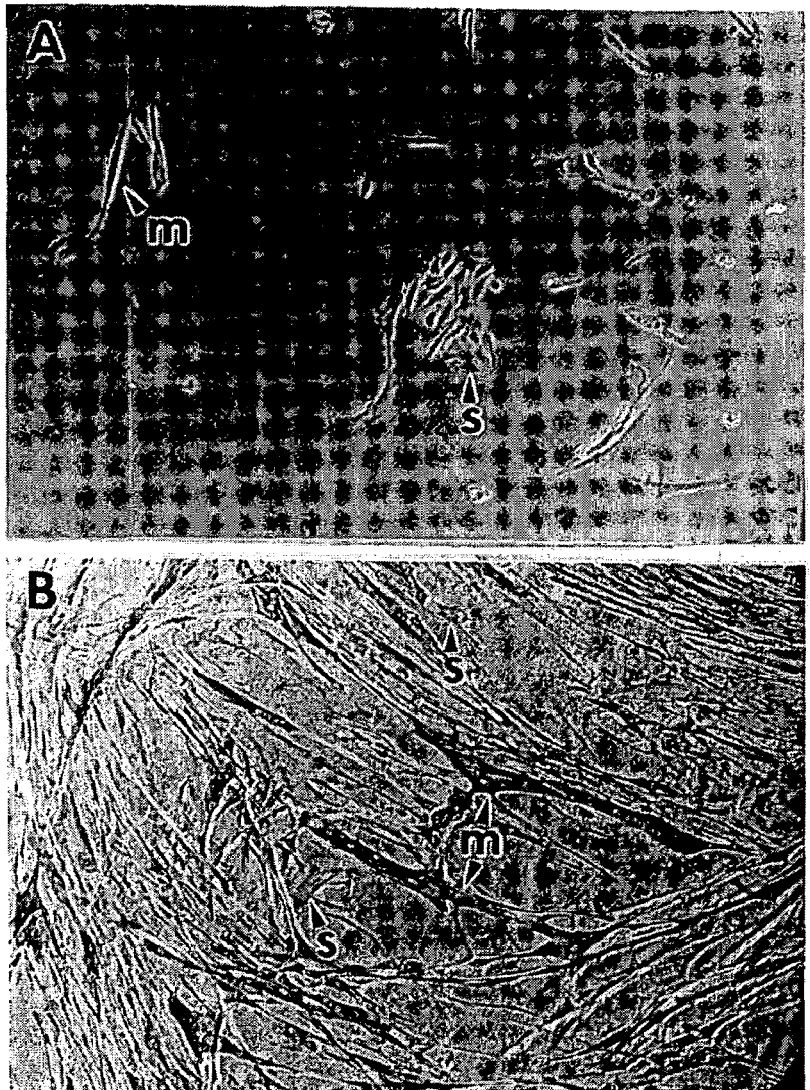
Figure 1. Pluripotent adult stem cell cultures derived from adult human skeletal muscle. Original magnification = 40x. s = stellate shaped cells. m = bipolar cell/small myotube. A. Primary culture at 3 days in culture. Phase contrast. B. Secondary culture (PPASCs) treated for one week with dexamethasone at $10^{-8}$ M and stained with MF-20, an antibody to sarcomeric myosin.

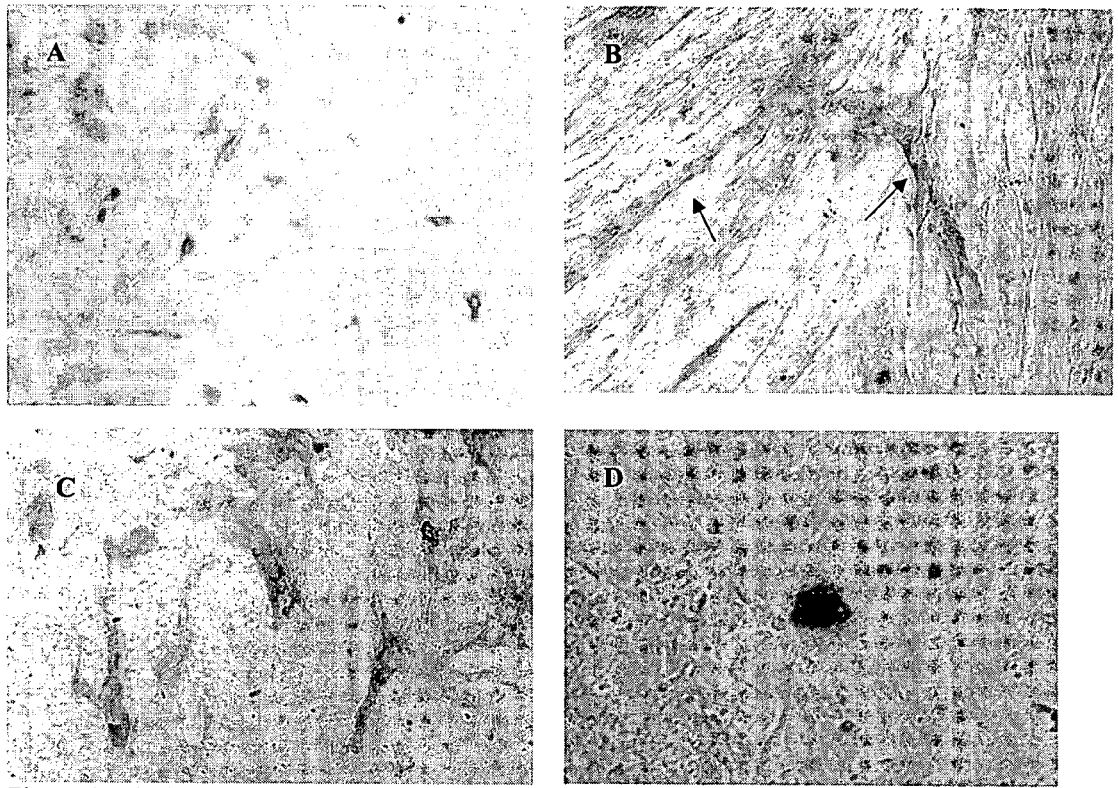

Figure 2: Pluripotent Adult Stem Cells isolated from human marrow and treated with dexamethasone in culture. A. $10^{-8}$ M dexamethasone treatment for 7 days and culture stained with antibodies to desmin. Myogenic precursor cells stain. Original magnification = 60x. B. Culture treated for 33 days with $10^{-10}$ M dexamethasone and stained with an antibody to the heavy chain of myosin. Skeletal muscle. Original magnification = 200x. Arrows point to stained multinucleated myotubes. C. Culture treated for 33 days with $10^{-7}$ M dexamethasone and stained with an antibody to smooth muscle α-actin. Smooth muscle. Original magnification = 100x. D. Culture treated for 33 days with $10^{-7}$ M dexamethasone and stained with an antibody to cardiac troponin T. Cardiomyocyte. Original magnification = 200x.

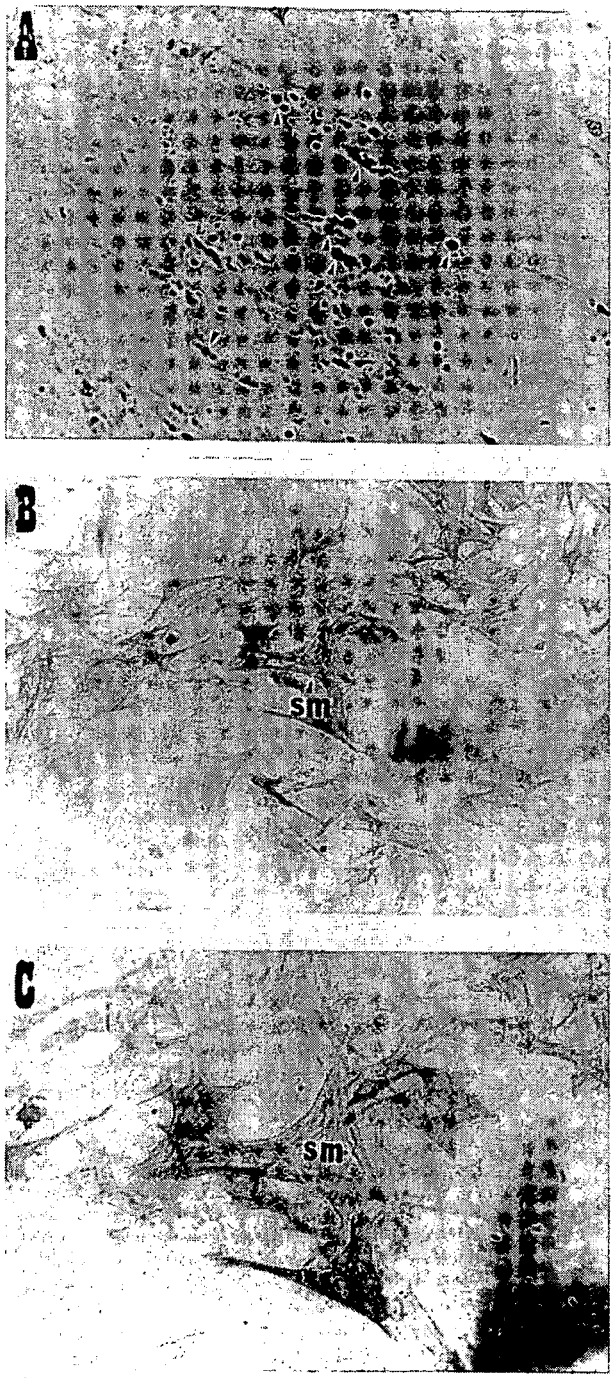

Figure 3. Pluripotent adult stem cell cultures derived from adult human skeletal muscle and treated with dexamethasone at $10^{-6}$ M dexamethasone for 4 weeks. A. Culture stained with Sudan Black B for neutral lipids. Arrows point to adipocytes. B and C. Cultures stained with antibody to smooth muscle $\alpha$-actin. Original magnification of B = 100x. Original magnification of C = 200x.

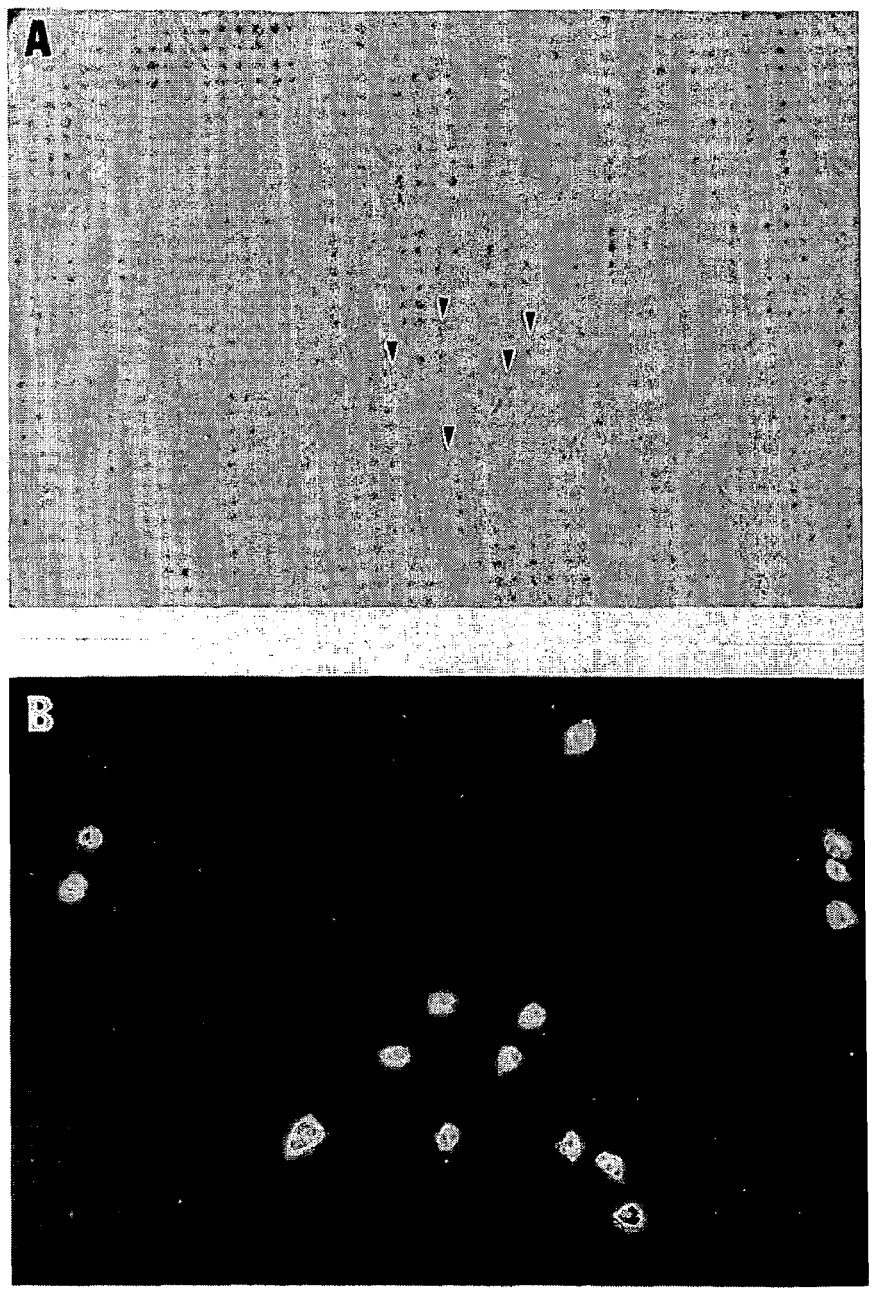
Figure 4. Pluripotent adult stem cell cultures derived from adult human skeletal muscle and treated with dexamethasone at $10^{-7}$ M dexamethasone for 4 weeks. Original magnification = 100x. A. Phase contrast. B. Fluorescence after cells were allowed to uptake acetylated LDL for 20 min.

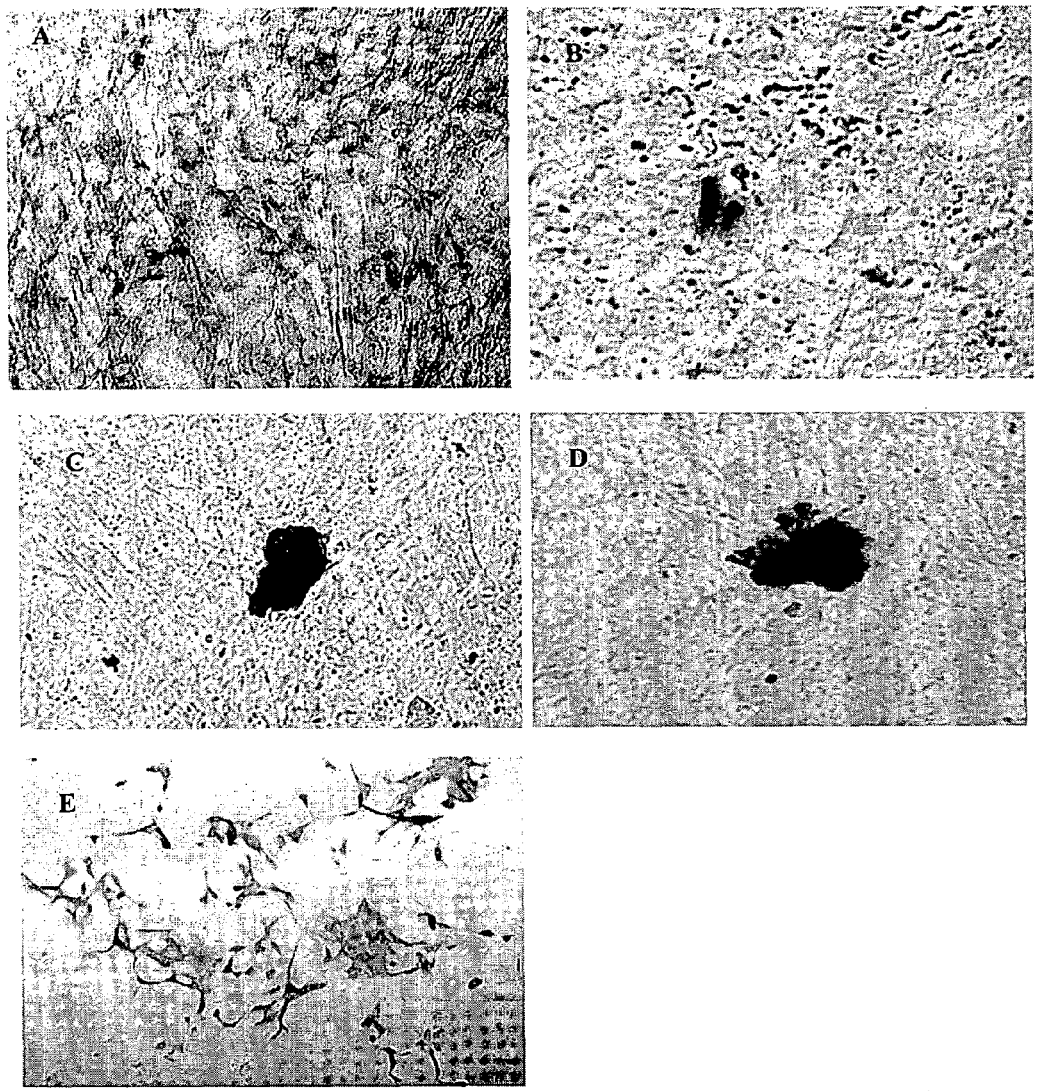

Figure 5: Pluripotent Adult Stem Cells isolated from human marrow and treated with dexamethasone in culture for 33 days. A. $10^{-6}$ M dexamethasone and stained with an antibody to human umbilical vein endothelial cells. Endothelial cells. Original magnification = 100x. B. $10^{-6}$ M dexamethasone stained with an antibody to IL-1β activated human umbilical vein endothelial cells. Endothelial cells. Original magnification = 150x. C. $10^{-8}$ M dexamethasone treated and stained with an antibody to bone sialoproteins I and II. Bone. Original magnification = 100x. D. $10^{-8}$ M dexamethasone and stained with an antibody to type II collagen. Cartilage. Original magnification = 100x. E.. $10^{-10}$ dexamethasone treated and stained with an antibody to talin. Fibroblasts. Original magnification = 60x.

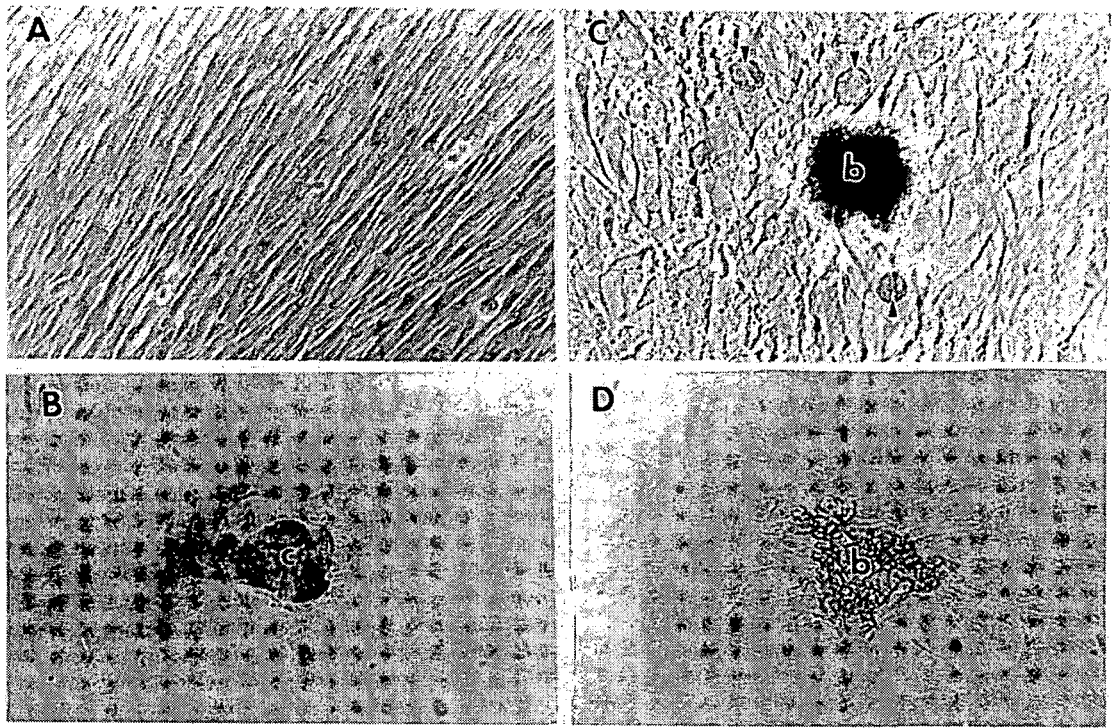

Figure 6. Pluripotent adult stem cell cultures derived from adult human skeletal muscle and treated with dexamethasone for 4 weeks. Original magnification = 60x  A. Phase contrast of spindle shaped cells growing in a swirl pattern. $10^{-8}$ M dexamethasone B. Nodule of cells stained with Alcian blue at pH 1.0.  c = cartilage. $10^{-9}$ M dexamethasone. C. Nodule of cells stained with Von Kossa's stain for mineral.  D. Nodule of cells stained with Von Kossa's after pretreatment with EDTA to remove calcium. $10^{-8}$ M dexamethasone.

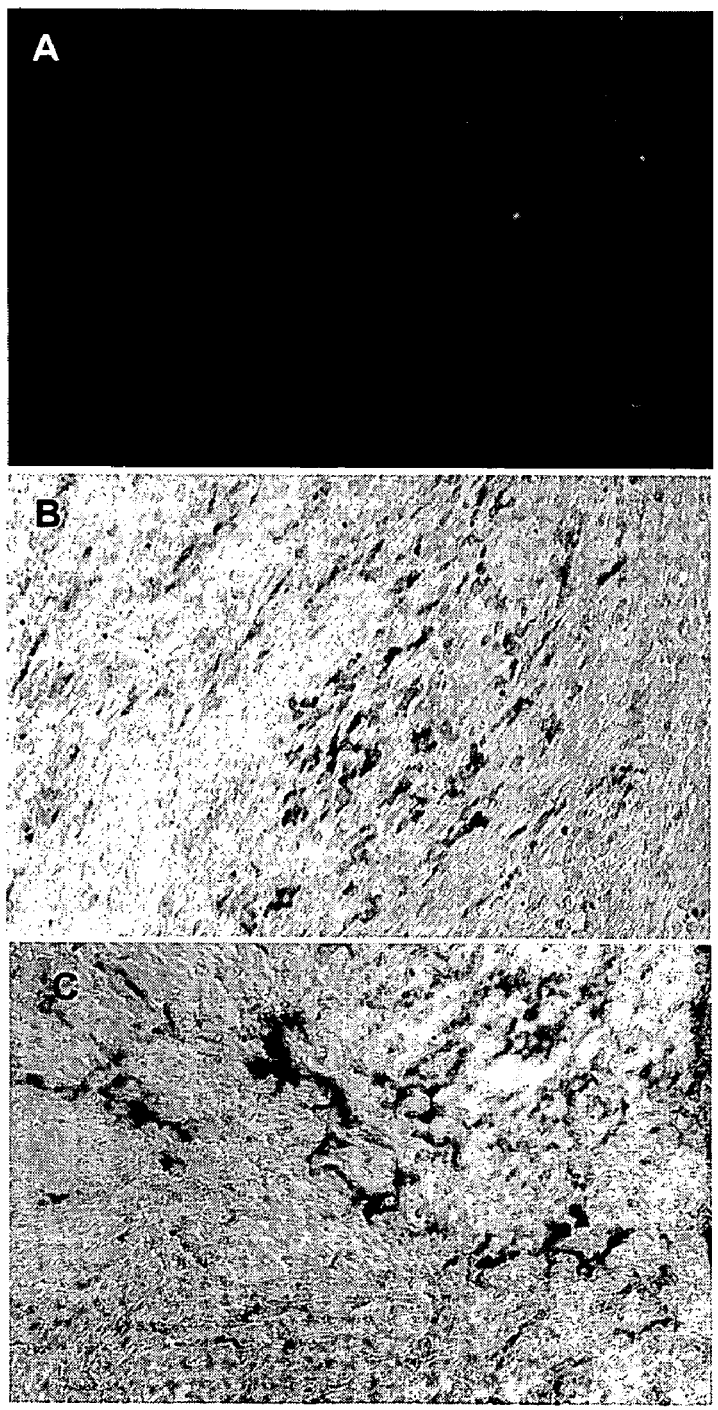

Figure 7: Pluripotent adult stem cell cultures derived from adult human skeletal muscle and treated with dexamethasone for 4 weeks. A. Culture treated with $10^{-10}$ M dexamethasone and stained with antibody to the 160 kD neurofilament Original magnification = 100x. B. Culture treated with $10^{-9}$ M dexamethasone and stained with antibody to GFAP. Original magnification = 40x. C. Culture treated with $10^{-8}$ M dexamethasone and stained with antibody to CNPase. Original magnification = 100x.

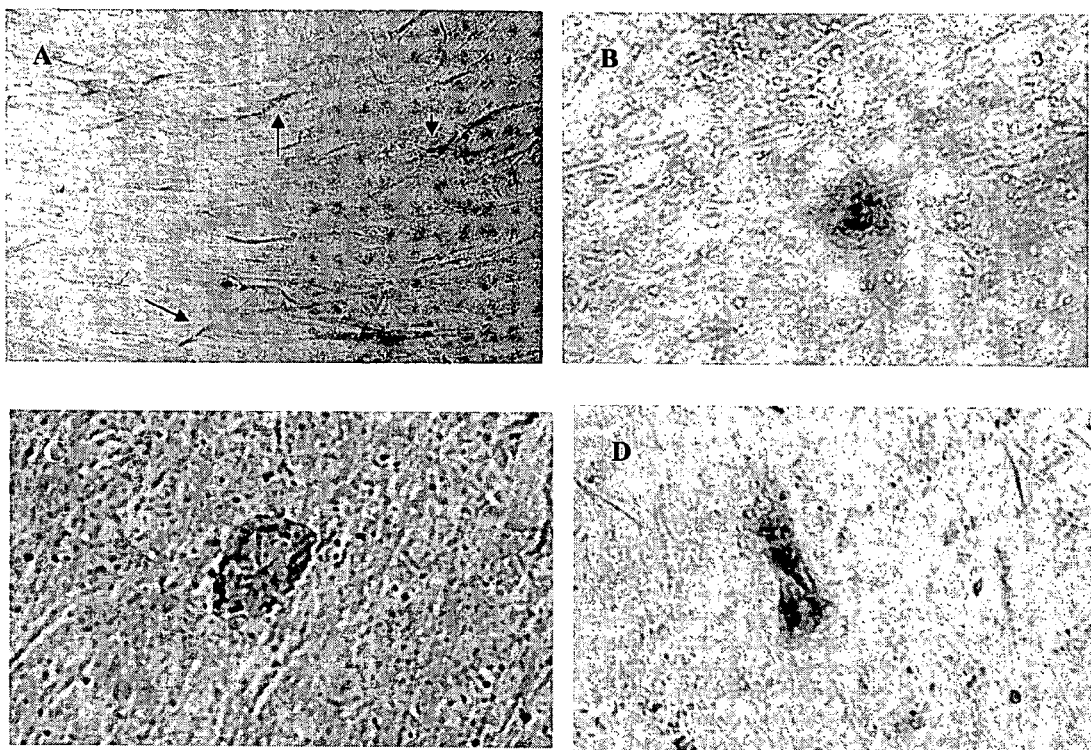

Figure 8. Pluripotent Adult Stem Cells isolated from human marrow and treated with dexamethasone in culture for 33 days. A. Treated with $10^{-10}$ M dexamethasone and stained with an antibody to CNPase. Glial cells. Original magnification = 60x. B. Treated with $10^{-7}$ M dexamethasone and stained with antibody H-4, against hepatocytes. Liver. Original magnification =200x. C. Treated with $10^{-6}$ M dexamethasone and stained with antibody OV-6 against hepatocytes. Liver. Original magnification = 200x. D. Treated with $10^{-7}$ M dexamethasone and stained with an antibody against -fetoprotein. Hepatocyte. Original magnification = 200x.

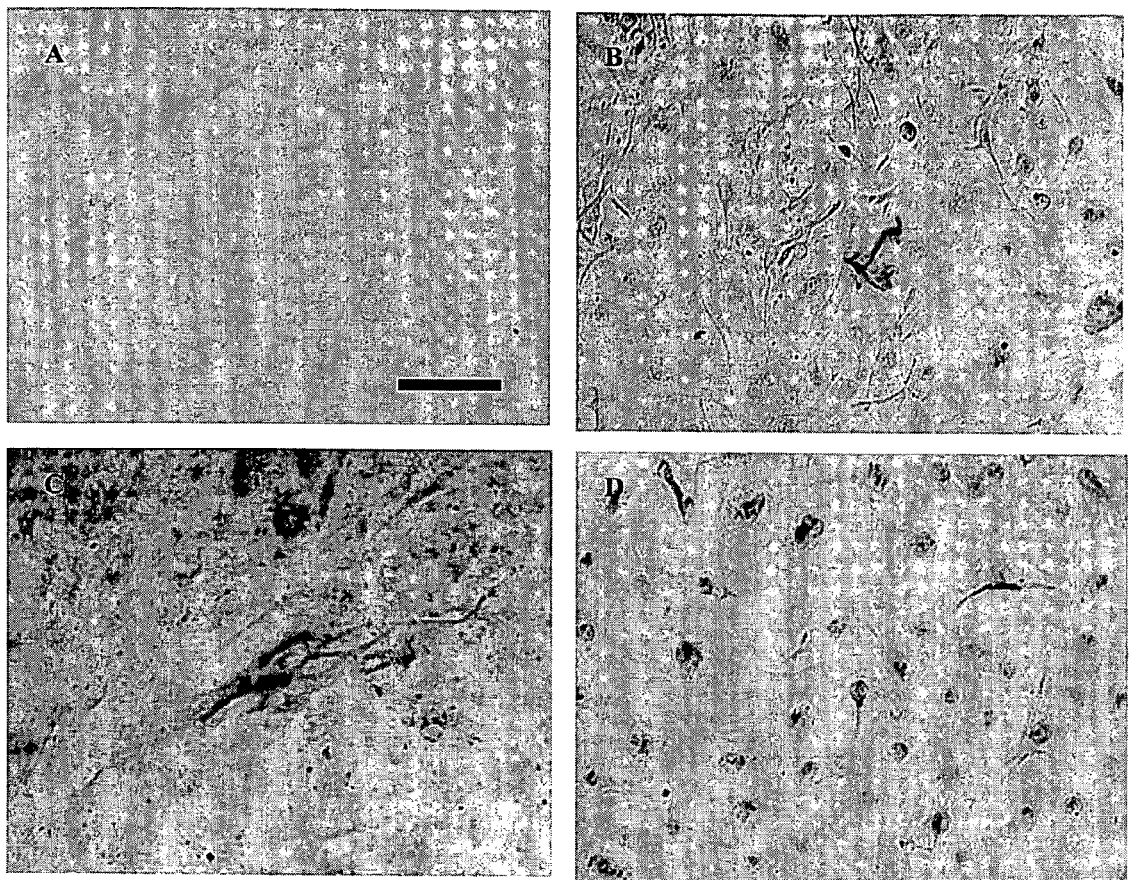
Figure 9. Human adult stem cells treated with neurococktail for 48 h: A. Without primary antibody, B. Anti-RT-97, C. Anti- β-tubulin-III, D. Anti-GFAP, The blue arrows point to cells that appear morphologically round. The black arrows point to the cells with elongated processes. The red arrows point to unstained cells. Scale bar, 10 μM.

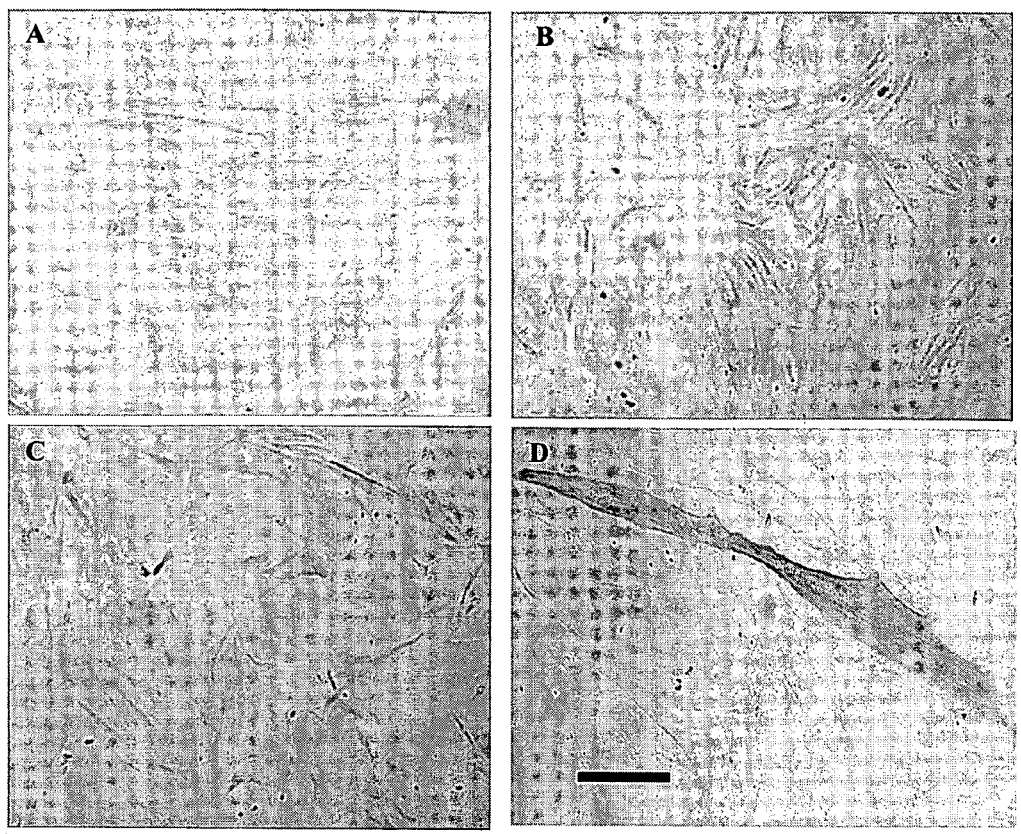
Figure 10. Human adult stem cells treated with neurococktail for 48 h: A. Control (no neurococktail) with anti-β-tubulin III antibody. B. Neurococktail treated cells with anti-β-tubulin III: C. Neurococktail treated cells with anti-desmin. D. Neurococktail treated cells with anti-MF20. Arrow points to nuclei within cell. Scale bar, 10 µM.

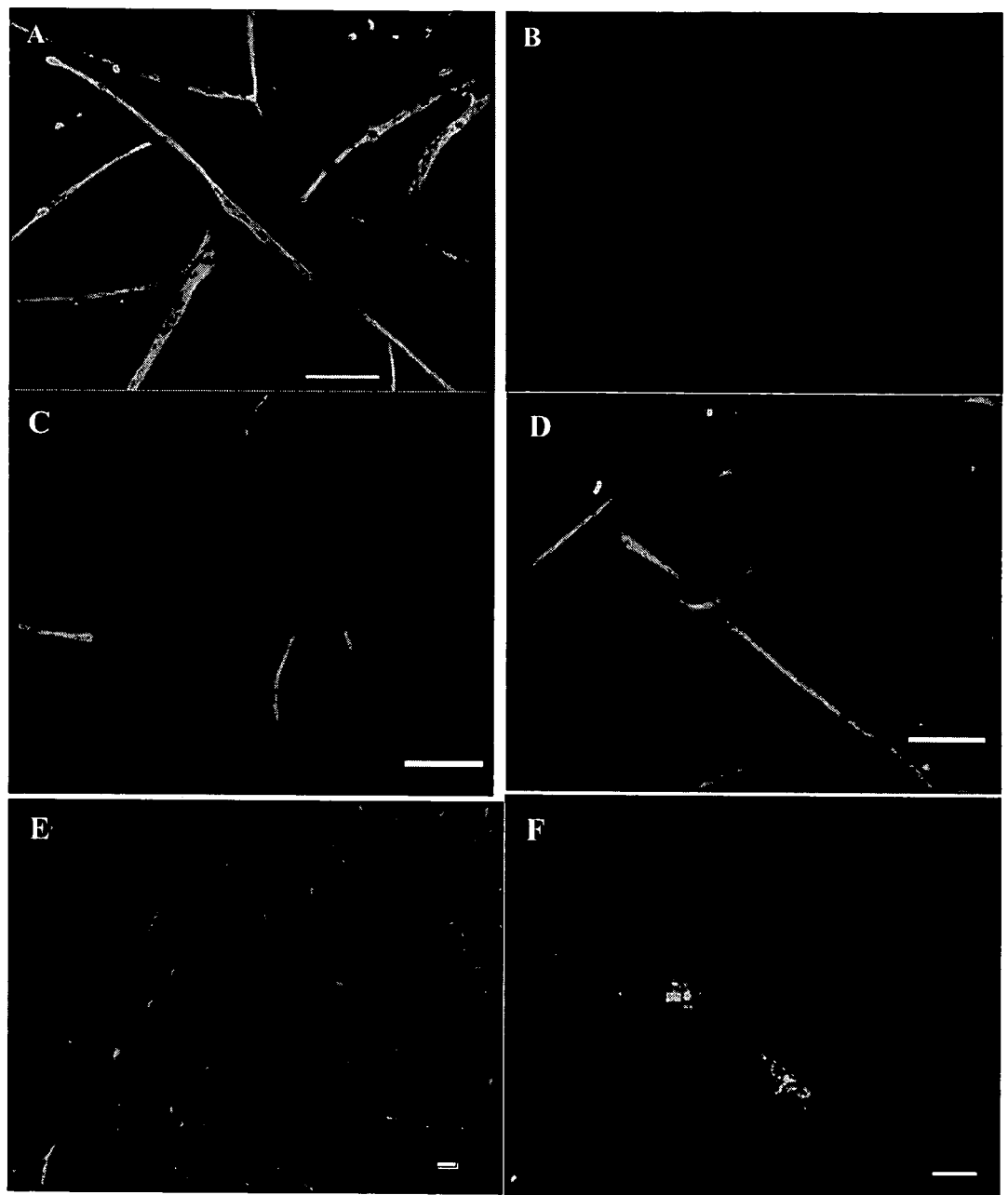
Figure 11. Human adult stem cells treated with neurococktail for 10 days: A. Control (GFAP antibody that was not positive), B. Anti-MF20. C. Anti-HSMV, D. Anti- anti-NF200. E. Anti -β-tubulin III, and F. Anti-synapsin. Scale bar, 10 μM.

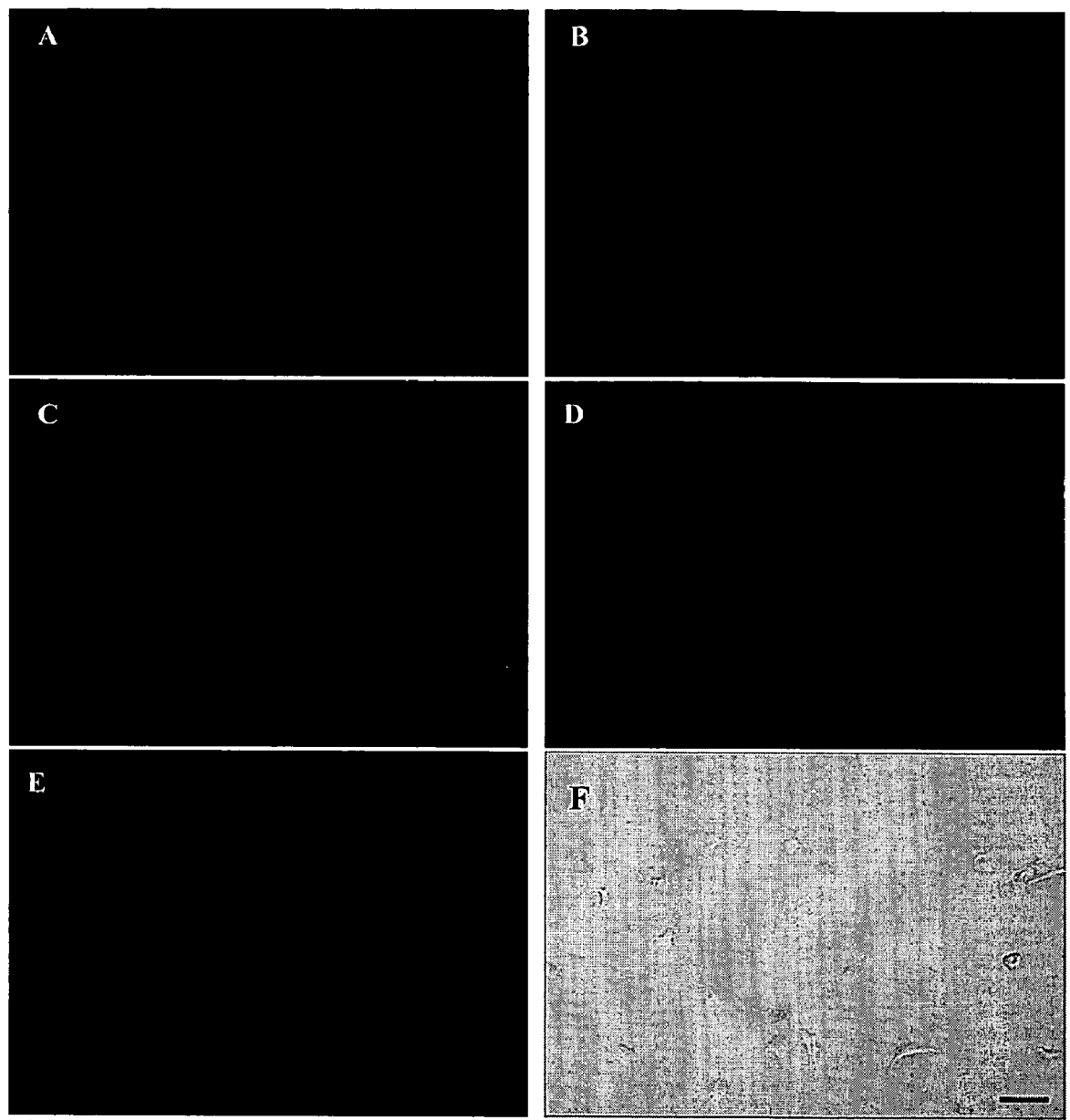
Figure 12. Human adult stem cells treated with neurococktail for 48 h then treated with Calcium Green. Glutamate as added to the culture and pictures taken at the following time intervals: A. 0 minutes, B. 10 minutes, C. 30 minutes, D. 50 minutes, E. 60 minutes, and F. light picture at 60 min. Scale bar, 10 µM.

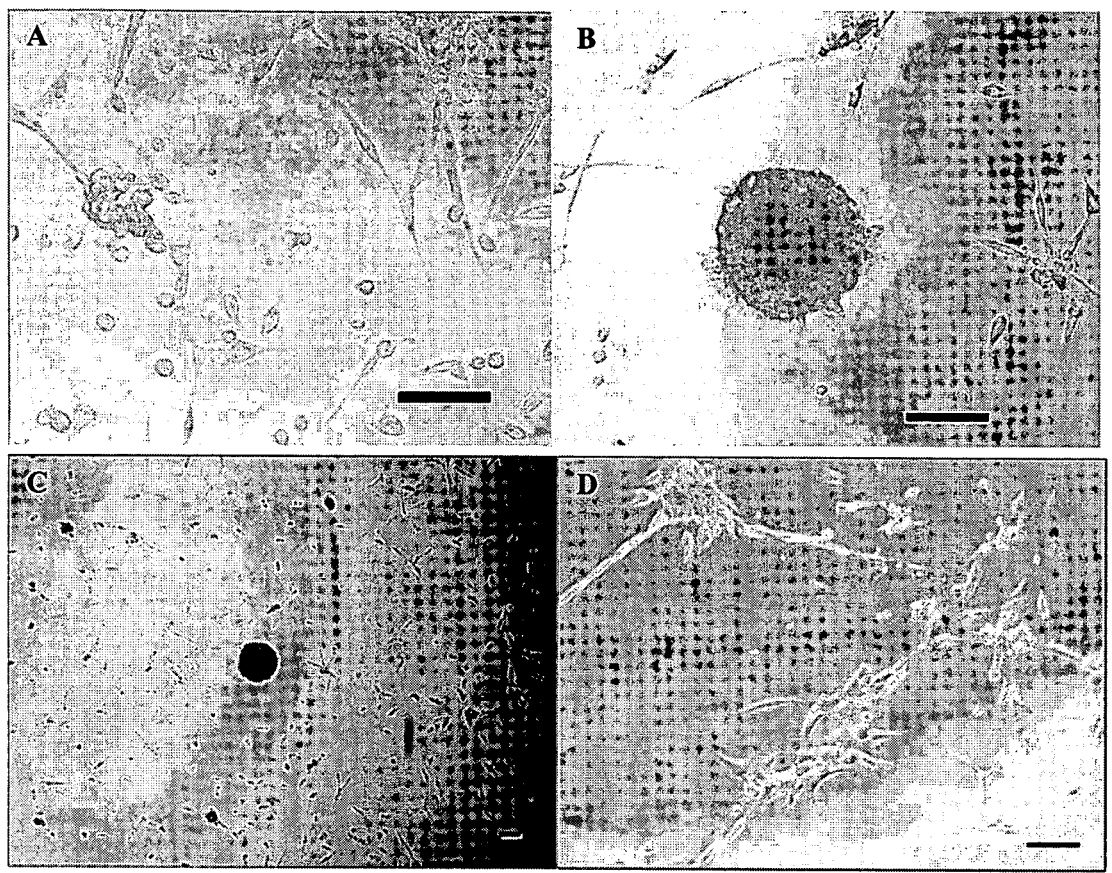
Figure 13. The human adult stem cells grown with the neurosphere protocol with the initial treatment with EGF and bFGF at A. Day 3 B. Day 11. Scale bar, 10 μM. The human adult stem cells treated with the neurosphere cocktail with EGF and bFGF for 14 days, addition of laminin for 24 hours, followed by addition of NT-3 growth factor at C. Day 17 (1 day with NT-3). D. Day 22 (5 days with NT-3). Scale bar, 10 μM.

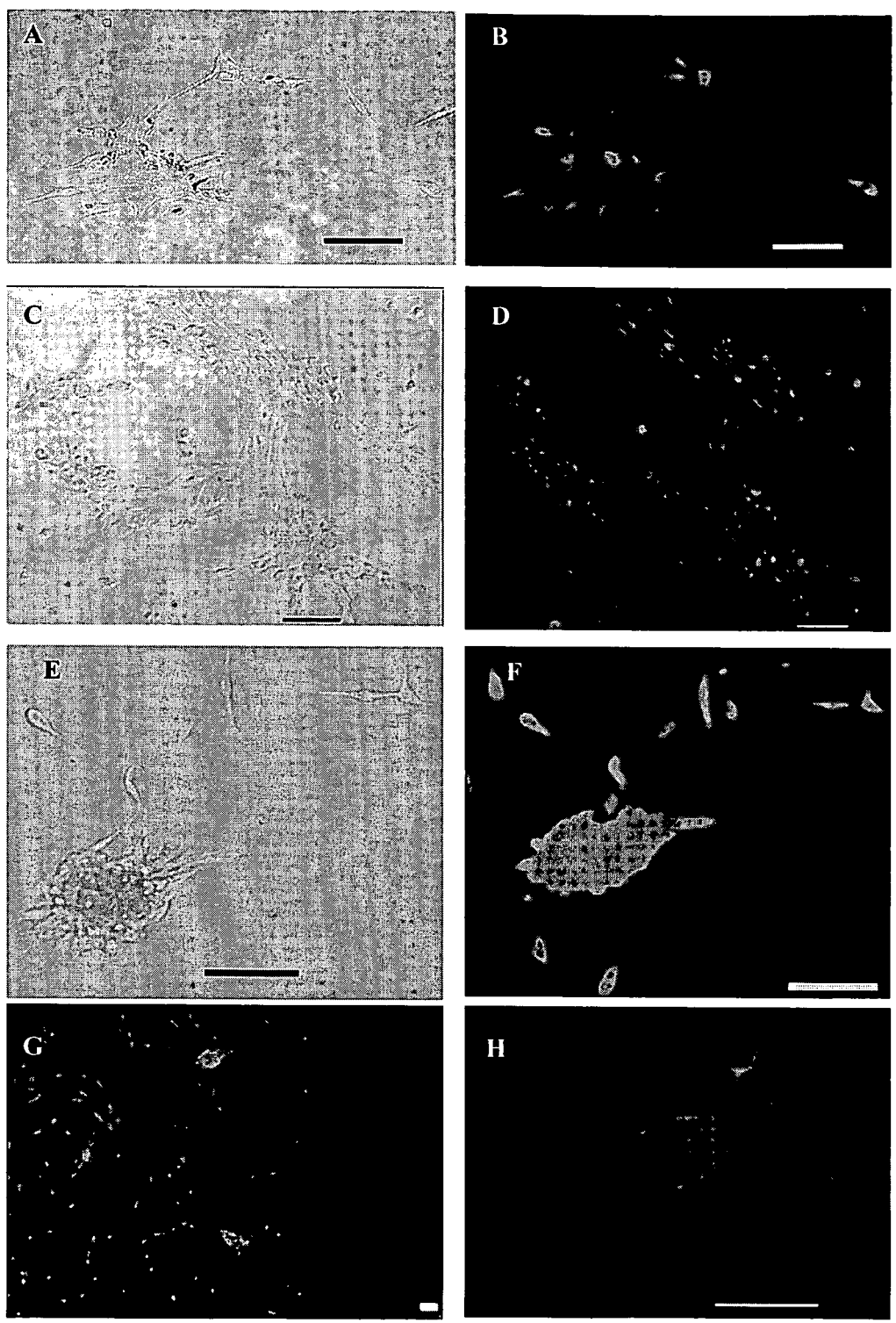
Figure 14. Human adult stem cell treated with the neurosphere protocol at Day 22 stained with anti-CNPase. A,C, E. Phase contrast microscopy. B,D,F,G,H. Fluorescent microscopy. White arrow points to more intense fluorescent cells, B. Scale bar, 10 μm

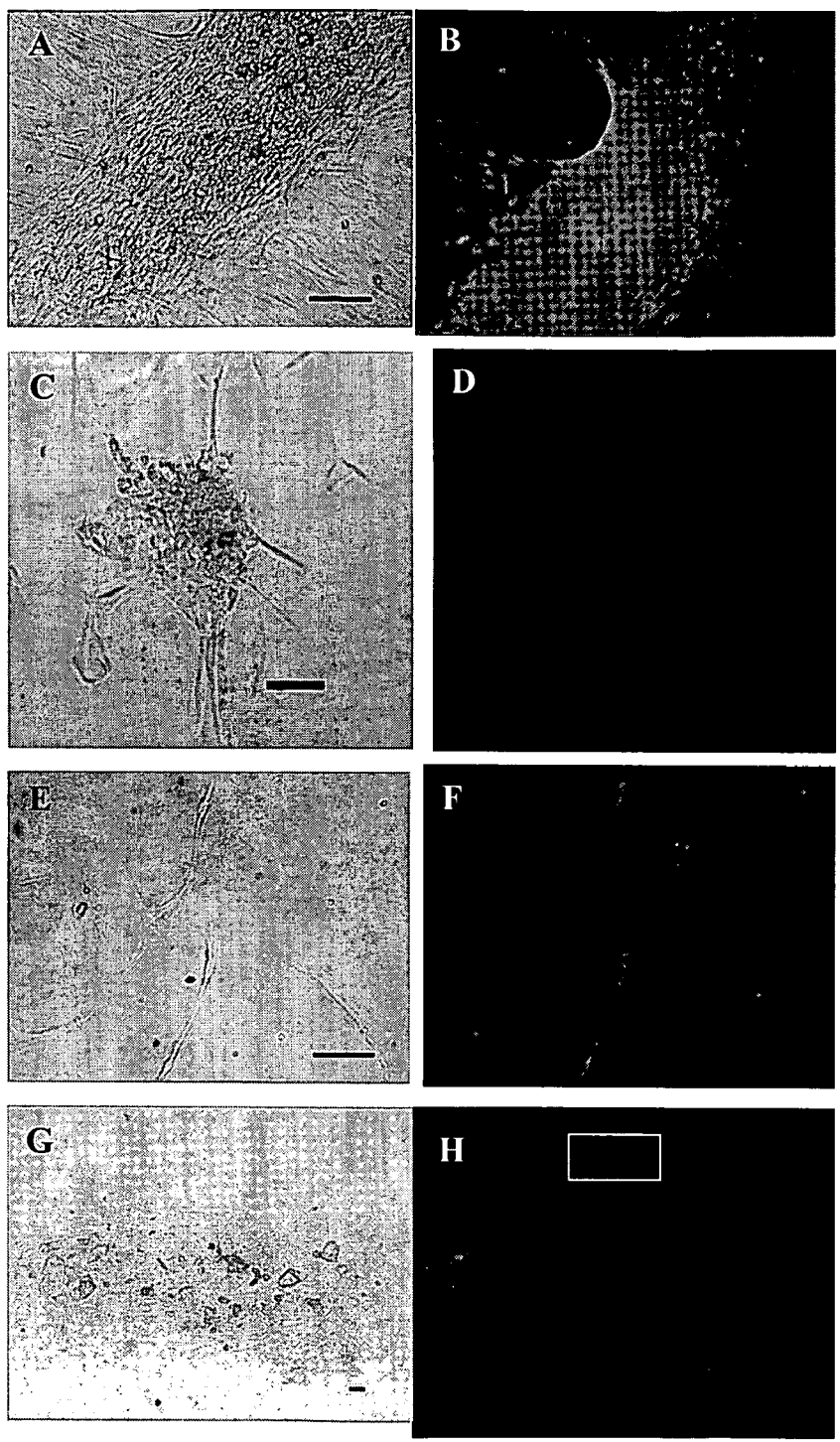
Figure 15. Human adult stem cells treated with the neurosphere protocol at Day 22 treated with antibody to β-tubulin III. A, C. Phase contrast microscopy. B, D. Fluorescent microscopy. Stained with antibody to 160 kD neurofilament. E. Phase contrast F. Fluorescent microscopy. Treated with antibody to GFAP. G Phase contrast. H. Fluorescent microscopy. Scale bar, 10 μm.

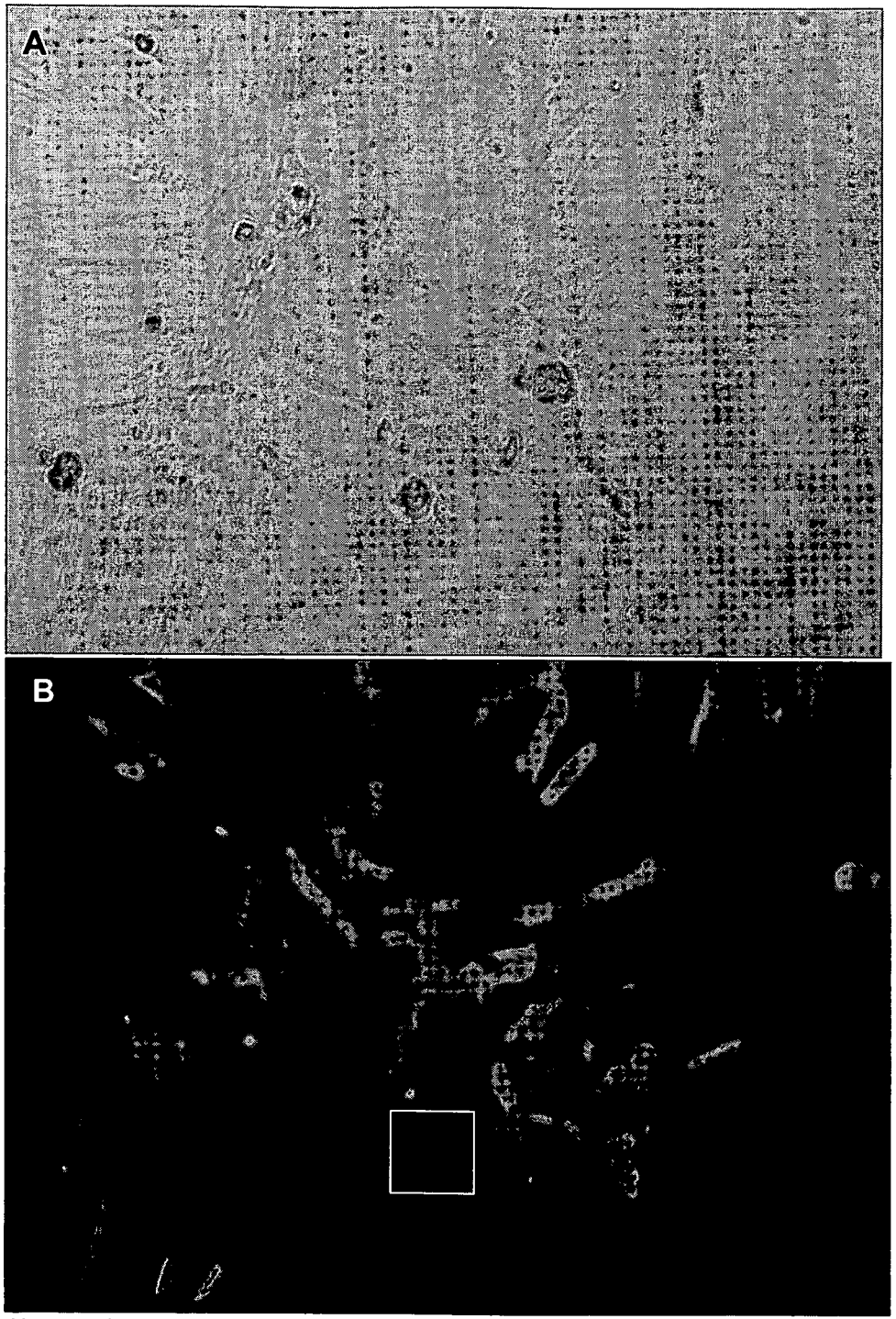
Figure 16. Human adult stem cells treated with the neurosphere protocol at Day 22 treated with antibody to desmin. A. Phase contrast. B. Fluorescent. The box represents areas where there was a cell but no fluorescence.

PLURIPOTENT ADULT STEM CELLS

This application claims priority, under 35 U.S.C. Section 119, from U.S. Provisional Application Ser. No. 60/572,494 filed May 20, 2004, the disclosure of which is hereby incorporated herein by reference.

The invention relates to the field of adult stem cells and uses thereof.

BACKGROUND

Regeneration of tissue lost to disease or trauma is a goal of medicine. Such tissue losses—cartilage due to osteoarthritis, spinal nerves due to trauma, islet cells due to diabetes, cardiac muscle due to infarction, etc—cost hundreds of millions of dollars a year in addition to the lost quality of life of the patients. Embryonic stem cells have captured the news as a source of stem cells for tissue regeneration. The ethical problems are well known, but there are also less well-known problems such as tissue rejection, tumor formation, and inability to direct the differentiation of the cells.

Several research groups have been investigating the possibility of using non-embryonic stem cells, i.e., stem cells isolated from post-natal animals. The challenge associated with such stem cells is that they may not be able to differentiate in all three germ lineages, endodermal, mesodermal and ectodermal lineages. For example, the differentiation of some of the previously reported post-natal stem cells seems to be limited to mesodermal lineage. Additionally, some of the cells have a finite lifetime, which limits their usefulness when large numbers of cells are needed or if the regenerated tissue needs to last for 20 or more years.

Therefore, there is a need in the art for adult stem cells that have the ability to differentiate into all three lineages and that have indefinite propagation potential. Applicants have now isolated and characterized such cells.

SUMMARY OF THE INVENTION

The invention relates to a pluripotent adult stem cells and uses thereof.

In one aspect of the invention, pluripotent human adult stem cells expressing CD13, CD34 (while proliferating), CD56 and CD117, and not expressing CD10 and compositions comprising such cells are provided.

In another aspect, differentiated cells of ectodermal, endodermal, or mesodermal lineage obtained by differentiation from the stem cells of the invention, and compositions comprising such cells, are also provided.

In yet another aspect of the invention, methods of use of the stem cells of the invention are provided.

BRIEF DESCRIPTION OF THE DRAWINGS

FIGS. 1A-B represent: Pluripotent adult stem cell cultures derived from adult human skeletal muscle. Original magnification=40×. s=stellate shaped cells. M=bipolar cell/small myotube. A. Primary culture at 3 days in culture. Phase contrast. B. Secondary culture (PPASCs) treated for one week with dexamethasone at $10^{-8}$ M and stained with MF-20, an antibody to sarcomeric myosin.

FIGS. 2A-D represent: Pluripotent Adult Stem Cells isolated from human marrow and treated with dexamethasone in culture. A. $10^{-8}$ M dexamethasone treatment for 7 days and culture stained with antibodies to desmin. Myogenic precursor cells stain. Original magnification=6×. B. Culture treated for 33 days with $10^{-8}$ M dexamethasone and stained with an antibody to the heavy chain of myosin. Skeletal muscle. Original magnification=200×. Arrows point to stained multinucleated myotubes. C Culture treated for 33 days with $10^{-7}$ M dexamethasone and stained with an antibody to smooth muscle α-actin. Smooth muscle. Original magnification=100×. D. Culture treated for 33 days with $10^{-7}$ M dexamethasone and stained with an antibody to cardiac troponin T. Cardiomyocyte. Original magnification=200×.

FIGS. 3A-C represent: Pluripotent adult stem cell cultures derived from adult human skeletal muscle and treated with dexamethasone at $10^{-6}$ M dexamethasone for 4 weeks. A. Culture stained with Sudan Black B for neutral lipids. Arrows point to adipocytes. B and C. Cultures stained with antibody to smooth muscle α-actin. Original magnification of B=100×. Original magnification of C=200×.

FIGS. 4A-B represent: Pluripotent adult stem cell cultures derived from adult human skeletal muscle and treated with dexamethasone at $10^{-7}$ M dexamethasone for 4 weeks. Original magnification=100×. A. Phase contrast. B. Fluorescence after cells were allowed to uptake acetylated LDL for 20 min.

FIGS. 5A-E represent: Pluripotent Adult Stem Cells isolated from human marrow and treated with dexamethasone in culture for 33 days. A. $10^{-6}$ M dexamethasone and stained with an antibody to human umbilical vein endothelial cells. Endothelial cells. Original magnification=100×. B. $10^{-6}$ M dexamethasone stained with an antibody to IL-1β activated human umbilical vein endothelial cells. Endothelial cells. Original magnification=150×. C. $10^{-8}$ M dexamethasone treated and stained with an antibody to bone sialoproteins I and II. Bone. Original magnification=100×. D. $10^{-8}$ M dexamethasone and stained with an antibody to type II collagen. Cartilage. Original magnification=100×. E. $10^{-10}$ dexamethasone treated and stained with an antibody to talin. Fibroblasts. Original magnification=60×.

FIGS. 6A-D represent: Pluripotent adult stem cell cultures derived from adult human skeletal muscle and treated with dexamethasone for 4 weeks. Original magnification=60×. A. Phase contrast of spindle shaped cells growing in a swirl pattern. $10^{-8}$ M dexamethasone B. Nodule of cells stained with Alcian blue at pH 1.0. c=cartilage. $10^{-9}$ M dexamethasone. C. Nodule of cells stained with Von Kossa's stain for mineral. D. Nodule of cells stained with Von Kossa's after pretreatment with EDTA to remove calcium. $10^{-8}$ M dexamethasone.

FIGS. 7A-C represent: Pluripotent adult stem cell cultures derived from adult human skeletal muscle and treated with dexamethasone for 4 weeks. A. Culture treated with $10^{-10}$ M dexamethasone and stained with antibody to the 160 KD neurofilament. Original magnification=100×. B. Culture treated with $10^{-9}$ M dexamethasone and stained with antibody to GFAP. Original magnification=40×. C. Culture treated with $10^{-8}$ M dexamethasone and stained with antibody to CNPase. Original magnification=100×.

FIGS. 8A-D represent: Pluripotent Adult Stem Cells isolated from human marrow and treated with dexamethasone in culture for 33 days. A. Treated with $10^{-10}$ M dexamethasone and stained with an antibody to CNPase. Glial cells. Original magnification=60×. B. Treated with $10^{-7}$ M dexamethasone and stained with antibody H-4, against hepatocytes. Liver. Original magnification=200×. C. Treated with $10^{-6}$ M dexamethasone and stained with antibody OV-6 against hepatocytes. Liver. Original magnification=200×. D. Treated with $10^{-7}$ M dexamethasone and stained with an antibody—fetoprotein. Hepatocyte. Original magnification=200×.

FIGS. 9A-D represent: Human adult stem cells treated with neurocoktail for 48 h: A. Without primary antibody, B. Anti-RT-97, C. Anti-β-tubulin-III, D. Anti-GFAP, The blue arrows point to cells that appear morphologically round. The black arrows point to the cells with elongated processes. The red arrows point to unstained cells. Scale bar, 10 μM.

FIGS. 10A-D represent: Human adult stem cells treated with neurocoktail for 48 h: A. Control (no neurocoktail) with anti-β-tubulin III antibody. B. Neurocoktail treated cells with anti-β-tubulin III: C. Neurocoktail treated cells with anti-desmin. D. Neurocoktail treated cells with anti-MF20. Arrow points to nuclei within cell. Scale bar, 10 μM.

FIGS. 11A-F represent: Human adult stem cells treated with neurocoktail for 10 days: A. Control (GFAP antibody that was not positive), B. Anti-MF20. C. Anti-HSMV, D. Anti-anti-NF200. E. Anti-β-tubulin III, and F. Anti-synapsin. Scale bar, 10 μM.

FIGS. 12A-F represent: Human adult stem cells treated with neurocoktail for 48 h then treated with Calcium Green. Glutamate as added to the culture and pictures taken at the following time intervals: A. 0 minutes, B. 10 minutes, C. 30 minutes, D. 50 minutes, E. 60 minutes, and F. light picture at 60 min. Scale bar, 10 μM.

FIGS. 13A-D represent: The human adult stem cells grown with the neurosphere protocol with the initial treatment with EGF and bFGF at A. Day 3 B. Day 11. Scale bar, 10 μM. The human adult stem cells treated with the neurosphere cocktail with EGF and bFGF for 14 days, addition of laminin for 24 hours, followed by addition of NT-3 growth factor at C. Day 17 (1 day with NT-3). D. Day 22 (5 days with NT-3). Scale bar, 10 μM.

FIGS. 14A-H represent: Human adult stem cell treated with the neurosphere protocol at Day 22 stained with anti-CNPase. A, C, E. Phase contrast microscopy. B,D,F,G, H. Fluorescent microscopy. White arrow points to more intense fluorescent cells, B. Scale bar, 10 μM.

FIGS. 15A-H represent: Human adult stem cells treated with the neurosphere protocol at Day 22 treated with antibody to β-tubulin III. A, C. Phase contrast microscopy. B, D. Fluorescent microscopy. Stained with antibody to 160 kD neurofilament. E. Phase contrast. F. Fluorescent microscopy. Treated with antibody to GFAP. G. Phase contrast. H. Fluorescent microscopy. Scale bar, 10 μM.

FIGS. 16A-B represent: Human adult stem cells treated with the neurosphere protocol at Day 22 treated with antibody to desmin. A. Phase contrast. B. Fluorescent. The box represents areas where there was a cell but no fluorescence.

DETAILED DESCRIPTION OF THE INVENTION

This invention relates to the isolation and characterization of unique stem cells that are available in adults. As used herein "adult" means post-fetal, i.e., an organism from the neonate stage through the end of life.

The adult stem cells of the invention offer significant advantages compared to embryonic stem cells, they: (i) do not have to be kept from differentiating (they are naturally quiescent unless stimulated by a signal); (ii) are autologous, obviating immunorejection (if isolated from the same patient who is to be treated); and (iii) never form tumors in vivo (if implanted sub-cutaneously, they form loose connective tissue and fat; in other tissues they respond to exogenous signals to form the tissue at that site).

The stem cells of the invention are pluripotent. As used herein, the term "pluripotent stem cells" means that the cells are capable of differentiating into tissues of all three germ or dermal layers—mesoderm, endoderm, and ectoderm. The stem cells of the present invention are hence referred to as "Pluripotent Adult Stem Cells" or PPASCs for short. The PPASCs of the invention are isolated cells, i.e., this term does not refer to cells as they are found in the nature.

The differentiation potential of the PPASCs of the invention is such that a treatment with a single compound, dexamethasone, (e.g. single culture condition) can induce cells to differentiate into phenotypes of more than one lineage. When PPASCs were treated with dexamethasone, skeletal muscle, smooth muscle, endothelial cells, fibroblasts, marrow stromal fibroblasts, epithelial cells, cartilage, bone, cardiac myocytes, fat cells, neurons, astrocytes, oligodendrocytes, and hepatocytes were induced (see e.g. Examples). Dexamethasone may be used in a range of concentrations, for example, $10^{-9}$ M to $10^{-6}$ M. Depending on the desired differentiation phenotype, the concentration of dexamethasone may be manipulated to favor a particular phenotype (but not fully exclude the others) (see e.g. Example).

The ability of PPASCs to differentiate as described above represent a considerable advantage of the stem cells of the invention. Frequently, the use of specific culture conditions for each phenotype, and/or in vivo cell tracking, are required to show the differentiation potential of cells. The disadvantage of using specific culture conditions is that such conditions may be favoring a small subset of single lineage committed cells at the expense of any other cells. In other words, under such circumstances, it is difficult to determine if the cells are pluripotent or whether the population contains a mixed population of progenitor cells. Similarly, when in vivo studies are used, it is difficult to determine if the labeled cells seen in the tissue are derived from a pluripotent cell or from a mixed population of progenitor cells.

In addition to being capable of differentiating into phenotypes, or tissues, from all three dermal layers, the PPASCs seem to have an unlimited proliferation potential. This means that a small tissue biopsy will yield enough cells, after expansion in culture, to accomplish any regenerative task. For example, PPASCs are present in a number of tissues: skeletal muscle, bone marrow, skin, liver, and brain; and while the liver and brain are not sources that one would wish to use for tissue engineering, skeletal muscle, skin and bone marrow lend themselves to biopsy. In particular, skeletal muscle can be obtained in an outpatient procedure with a minimal morbidity.

The human PPASCs of the invention express CD13, CD34 (while proliferating), CD56 and CD117, and do not express CD10. As described herein, PPASCs are contact inhibited and they stop expressing CD34 when they stop proliferating. The cells also do not express CD2, CD5, CD 14, CD19, CD33, CD45, and DRII; and are Lin (hematopoietic lineage markers) negative. Additionally, the human PPASCs do not express the stage specific embryonic antigen SSFA-2. In the preferred embodiments, the cells are derived from human bone marrow or human skeletal muscle and have the CD profile as described in Table 4. For example, the cells are positive for CD13, CD34 (while proliferating), CD56, CD117, CD90 and nestin, and negative for CD3, CD10, CD14, CD16, CD31, CD33, CD64, and stro-1. The CD profiling of PPASCs isolated from a human skeletal muscle and a human bone marrow is described in the Examples.

The PPASCs may be isolated according to the procedure described for the rat in Lucas et al., A population of cells resident within embryonic and newborn rat skeletal muscle is capable of differentiating into multiple mesodermal phenotypes; Wound Repair and Regeneration, 3: 449-460, (1995), hereby incorporated herein by reference, and as detailed in the Examples.

The PPASCs can be maintained in culture as described in the Examples. In one embodiment, the PPASCs are maintained in EMEM medium supplemented with 10% pre-selected horse serum (pre-selected as described in the Examples). However, a person of skill in the art may be able to make changes, or design and utilize other culture media, including a serum-free media, and/or conditions by altering the conditions and monitoring the effect of such changes of the CD profile of stem cells. Advantageously, the PPASCs do not require the presence of the anti-differentiation factor or leukemia inhibitory factor in the culture media. However, the PPASCs are contact inhibited and this should be taken into consideration when culturing the cells.

Also within the scope of the invention are compositions comprising PPASCs, e.g. pharmaceutical compositions comprising a therapeutically effective amount of PPACS.

The invention further relates to methods of use of the PPASCs, e.g., methods of treatment and/or tissue/organ repair by administering PPASCs or differentiated cells derived therefrom. Autologous or allogenic PPASCs may be used. Appropriate differentiated cells (of ectodermal, mesodermal or endodermal lineage) may be derived from PPASCs using selected concentrations of dexamethasone or other factors that induce differentiation into a particular phenotype. The mode of administration can be determined by a person of skill in the art depending on the type of organ/injury to be treated. For example, PPASCs or differentiated cells derived therefrom, may be administered by injection (as a suspension) or implanted on a biodegradable matrix.

In one embodiment, PPASCs may be used for regeneration and repair of damaged organs or tissues. For example, PPASCs (isolated from the same patient or HLA-matched allogenic PPASCs) are seeded into a biocompatible, biodegradable matrix at a density of $1 \times 10^7$ cells per cubic centimeter and cultured undifferentiated in vitro until cell attachment is achieved. This construct of cells+matrix is then implanted at the site of the tissue/organ to be repaired. Examples include, but are not limited to, articular cartilage defects, either partial or full-thickness, meniscus, calvaria, and skin burns. An example of a matrix includes polyglycolic acid mesh. In certain embodiments, PPASCs may be pre-treated in vitro with appropriate factors to commit the cells to a particular phenotypic pathway or pathways of the tissue/organ to be repaired. For example, PPASCs may be pre-treated with bone morphogenetic protein to differentiate them into an osteogenic lineage for repair of large segmental defects in bone. Other examples of use include forming new breast tissue following mastectomy; repairing kidneys or intestines following trauma or diverticulitis, repairing tendons or ligaments following sports injury, treating spinal cord following trauma.

In another embodiment, the invention encompasses systemic distribution of stem cells for diseases that have a deficiency of precursor cells, such as osteoporosis or spinal cord injury. For example, PPASCs in suspension may be injected into the organ of interest or into the circulatory system, the number of cells injected being from $10^6$ to $10^9$ in an appropriate amount of physiological saline. Example of systemic injection for a systemic disease is osteoporosis, where an appropriate amount of the PPASCs would distribute to the bone and provide an adequate amount of osteoprogenitor cells. Pre-differentiated PPASCs may also be used.

In another embodiment, the PPASCs may be used as a vehicle for introducing genes to correct genetic defects, such as osteogenesis imperfecta. For example, a reservoir of the patient's PPASCs is isolated, expanded in culture, and aliquots are stored frozen. An aliquot of $10^6$ to $10^9$ cells is transduced or transfected with the desired gene using methods known in the art, suspended in physiological saline, and injected into the patient. The patient is then monitored at intervals. If and when the transfected or transduced gene is no longer expressed, a new aliquot is thawed and transfected/transduced with the gene of interest and then injected into the patient. The procedure may be repeated as needed.

PPASCs may also be used is cell assays, for example as a cell source for cell toxicity studies (to test the effect of test compounds on cell toxicity), to test teratogenic or carcinogenic effects of test compounds by treating the cells with the compound and observing and/or recording the compound's effects on the cells, e.g. effect on cellular differentiation.

While the preferred stem cells of the invention are those isolated from a human, stem cells having the characteristics described herein, and used as described herein, may be isolated from other mammals, e.g. mouse, rat, rabbit and non-human primates. Such cells and their uses are also within the scope of the invention.

The invention is further described in the following non-limiting examples.

EXAMPLES

Example 1

Materials and Methods

Institutional Review Board approval from New York Medical College was garnered prior to procurement of specimens. Specimens were obtained from intra-operative tissue samples obtained as surgical discards in open reduction internal fixation procedures, or (for two bone marrow samples) diagnostic procedures, performed by surgeons at Westchester Medical Center. Tissue samples were obtained from 12 subjects (Table 1). Ten subjects were male and two were female. Subjects ranged in age from seven days to 73 years old (median 35 years, mean 31.05 years). Tissue specimens consisted of primarily skeletal muscle ranging in size 1 to 10 ml. One specimen consisted of muscle and scar tissue, which after processing, was predominantly scar tissue. Three samples consisted of bone marrow. One specimen was foreskin from the seven day old subject. Two samples did not have viable cells after the enzymatic digestion and two samples became contaminated in culture on day 1.

Once harvested, the specimens were prepared according to the procedure for rat skeletal muscle as described by Lucas et al. 1995[1] (for citations, see end of the Example). In brief, the specimens were freed of any visible tendon, ligaments, nerve fibers, vessels, and bone. Each specimen was minced while in a solution of Eagle's Minimal Essential Media with Earle's salts (EMEM) (GIBCO, Grand Island, N.Y.) and 10% pre-selected horse serum (Sigma Chemical Co., St. Louis, Mo.). The solution was then centrifuged, and the remaining pellet was obtained after the supernatant was discarded.

The lot of pre-selected horse serum was chosen to reproduce the results obtained by Lucas et. al.[1] That is, samples of several lots of horse serum were obtained from different suppliers and then the cell isolation and dexamethasone assay of Lucas et al. was repeated, with the positive control being the lot of horse serum used in that study. The lot of horse serum that reproduced the results seen in that study was selected and the entire lot purchased and used in the current experiments. A person of skill in the art can pre-select the horse serum by isolating the cells as described herein and culturing them with dexamethasone as described herein until a serum lot that reproduces the results of Table 5 is identified. The pre-selection of the serum is important because some batches of the serum cause differentiation of PPASCs into fibroblasts or other differentiated cells.

Each pellet was digested in a solution of collegenase (CLS-I Worthington Biochemicals, Freehold, N.J.) and dipase (Colloborative Research, Bedford, Mass.). After centrifugation, the tissue was placed in EMEM with 10% pre-selected horse serum. This solution was filtered with a 20 μM Nitex and centrifuged again. The tissue pellet was re-suspended in EMEM with 10% pre-selected horse serum. This solution was plated at 100,000 cells per 10 mm on 100 mm culture dishes, pre-coated with 1% bovine gelatin (EM Sciences, Cherry Hill, N.J.).

Cells were given EMEM with 10% pre-selected horse serum every other day. After approximately 8 days, the cultures consisted of two populations: multinucleated myotubes and mononucleated cells. Each culture was trypsinized and filtered through 20 μm Nitex filter. This filtration removed the myotubes leaving only mononucleated cells. These cells were then frozen in aliquots of 1 ml containing $10^6$ cells in EMEM+10% pre-selected horse serum and 7.5% DMSO (Sigma). Cryopreservation was performed in freezing chambers (Fisher Scientific, Norcross, Ga.) to slow freeze the cells to −80° C. This freezing procedure was determined empirically to preserve the stem cells while eliminating any differentiated cells, such as smooth muscle and endothelial cells.

Secondary cultures were created by thawing the aliquots of the frozen cells after at least 24 hours in the freezer and plating them at 100,000 cells per 100 mm gelatin-coated dish for expansion or for the assays described below.

Assay for Phenotypes

Dexamethasone Assay

PPASCs were thawed or trypsinized from expansion cultures and plated at 20,000 cells per 16 mm well in 24-well gelatin-coated culture plates (Corning Glass Works, Corning, N.Y.). All wells contained EMEM and 10% pre-selected horse serum. The control group remained in this medium, while the experimental wells contained media supplemented with dexamethasone (Sigma). Dexamethasone used were logarithmic concentrations from $10^{-10}$ to $10^{-6}$ M. Cultures were fixed and assayed for phenotypes at one-week intervals up to five weeks.

Neurococktail.[2,3]

The neurococktail was applied to attached human adult stem cells to induce the formation of a monolayer of neural cells.[2-4] This experiment was conducted in a series of steps in which growth factors and chemicals were added with different media changes at specified time intervals. The control plate was rinsed with EMEM and 10% horse-serum each time the experimental plate had a media treatment added and removed. In the first step, at 70% confluence, the media of the experimental plate received 10 ng/ml of bFGF in the EMEM/horse-serum for 24 hours at 37° C. The plates were rinsed twice with Dulbecco's phosphate buffered saline (DPBS) (GIBCO BRL, Grand Island, N.Y.). Then the neurococktail was added for 5 hours. The neurococktail consisted of 5 μg/ml insulin, 2% dimethylsulfoxide, 2 mM valproic acid, 200 μM butylated hydroxyanisole, 25 mM KCl, 10 μM forskolin, and 1 μM hydrocortisone in EMEM. Next, the neurococktail was completely removed and EMEM with 10% horse-serum was added. The cells remained in the neurobasal media over 2 days and then immunohistochemistry was performed.

The Neurosphere Protocol[3,5]

The adult human stem cells used were frozen two times and passaged a total of 7 times. $2\times10^5$ and $1\times10^5$ of adult stem cells were thawed and suspended in the neurosphere cocktail in 35 mm dishes. The neurosphere protocol con-

TABLE 1

| Preparation | Sex | Age | Tissue | Size of sample | Total cells isolated for primary prep | Viability after freeze/thaw | % recovery after freeze/thaw |
| --- | --- | --- | --- | --- | --- | --- | --- |
| HfsSC-8 | M | 7 days | foreskin | 5 ml | $14.8 \times 10^6$ | 87% | 100% |
| HmSC-2 | M | 67 | muscle | 10 ml | $11.25 \times 10^6$ | 98% | 100% |
|  |  |  |  |  |  | 97% | 100% |
|  |  |  |  |  |  | 100% | 100% |
|  |  |  |  |  |  | 77% | 81% |
|  |  |  |  |  |  | 82% | 94% |
|  |  |  |  |  |  | 75% | 77% |
| HmSC-3 | M | 48 | muscle | 2 ml | $5.38 \times 10^6$ | dead |  |
| HmSC-4 | F | 15 | muscle | 2 ml | $2.2 \times 10^6$ | contam |  |
| HmSC-5 | M | 36 | muscle | 3 ml | $6.3 \times 10^6$ | contam |  |
| HmSC-6 | M | 39 | muscle | 2 ml | $3.3 \times 10^6$ | 84.20% | 100% |
|  |  |  |  |  |  | 36.40% | 119% |
|  |  |  |  |  |  | 85.70% | 66.80% |
| HmSC-7 | M | 8 | muscle | 2 ml | dead |  |  |
| HmSC-8 | M | 18 mo | scar | 1 ml | $8.67 \times 10^5$ |  |  |
| HmSC-9 | M | 19 | muscle | 10 ml | $2.23 \times 10^7$ | 24.10% | 82.20% |
|  |  |  |  |  |  | 53.70% | 101% |
|  |  |  |  |  |  | 118% | 108% |
| HmaSC-1 | M | 21 | marrow | 1 ml | $8.25 \times 10^5$ | 72.3% | 85.2% |
| HmaSC-3 | M | 12 | marrow | 2 ml | $3.93 \times 10^6$ | 68.2% | 28.6% |
| HmaSC-5 | F | 3 | marrow | 1.5 ml | $3.0 \times 10^6$ | 87.5% | 87.5% | sisted of Neurobasal A media (GIBCO BRL), B27 proliferation/cell expansion supplement, 1% antibiotic/antimycotic, 20 ng/ml epidermal growth factor (EGF) and 20 ng/ml basic fibroblastic growth factor (bFGF) (Sigma) (Table 2.[3,5,6] The floating neurospheres that formed received EGF and bFGF every 3-5 days for 15 days. Ten μM of forskolin and 0.1 mM of IBMX, a phosphodiesterase inhibitor, was added to the preliminary neurosphere cocktail to increase cyclic AMP in later experiments.[7] An increase in intracellular cAMP has been shown to promote neuronal signaling mechanisms.

24-well plates were coated with poly-L-ornithine (Sigma P4957) and/or fibronectin[2,8] or laminin.[9] Then the media and the floating groups of neurospheres within the media from the 35 mm dishes were removed from the culture and centrifuged at 300×g for 15 minutes. The collected neurospheres were plated into 2 of the coated wells. The cells that remained adherent to the original 35 mm dishes were trypsinized using 1:5 trypsin/DPBS and centrifuged at 800×g for 15 minutes and were also plated in a well. The cells were plated in Neurobasal A media, B27 supplement, antibiotic/antimycotic, 10 μM of forskolin, 0.1 mM of IBMX, and 20 ng/ml EGF and bFGF with 1 μg/ml laminin. Two days later, 20 ng/ml neurotrophin-3 (NT-3) was added. Six days after the addition of NT-3, the cells were analyzed by immunohistochemistry.[3,10]

Glutamate Sensitivity/Calcium Uptake.

Neurococktail treated cells were rinsed with sterile Hanks solution.[11,12] A 2 mM stock solution of Calcium Green™ in DMSO was diluted 1:200 in Hanks solution and added to the cells when the Hanks solution was removed. The cells remained in darkness at room temperature for 1 hour. Then the Calcium Green™ was removed and 60 mM glutamic acid in Hanks Solution was added. Photomicrographs were taken on the Olympus Inverted Scope Model IMT with a fluorescent attachment. Fields of neurons were photographed at time intervals of 10 minutes, from 0 minutes up to an hour.

Immunohistochemistry:

The immunohistochemical protocol typically used was adopted from Romero-Ramos et al. (2002)[3]:

1) First, the cells were washed three times in PBS.
2) 0.5 ml of gluteraldehyde/paraformaldehyde was added for 5 minutes.
3) Three PBS rinses.
4) 0.25 ml of 0.3% $H_2O_2$ in 0.1% Triton X-100 in PBS was added for 10 minutes for samples that would have horseradish peroxidase. For samples using fluorescent labeled antibodies, this step was omitted.
5) Three PBS rinses.
6) 0.25 ml of 1% Goat Serum in 0.5% Tween-20 in PBS was used for 30 minutes at 37° C., serving as a blocker.
7) Following the goat block was three PBS rinses.
8) 0.25 ml of the primary antibody in PBS was added for 60 minutes at 37° C.
Antibodies used: Table 2
9) Then the wells were washed three times with PBS.
10) A second blocking step of 1% Goat Serum in PBS with 0.5% Tween was performed for 20 minutes preceding the addition of the secondary antibody.
11) The cells received 0.25 ml of horse-radish peroxidase conjugated IgG secondary antibody that was diluted with PBS to a concentration of 1:1500 or secondary antibody conjugated with either FITC or TRITC fluorochrome.
12) After 30 minutes of incubation at 37° C. with the secondary antibody, the wells were rinsed with PBS five times. If the secondary antibody was conjugated to fluorochrome, photographs were taken after this step.
13) 0.25 ml of True Blue or DAB solution was added and light protected for up to 20 minutes.
14) Five rinses of $dH_2O$ followed.
15) Photographs were taken on an Olympus Inverted Scope Model IMT light microscope.

TABLE 2

| Antibody | Antigen |
|---|---|
| Mesodermal Phenotypes: | |
| Anti-desmin | Different muscle phenotypes |
| MF20 | Sarcomeric myosin of muscle |
| Anti-MY32 | Fast chain to myosin muscle |
| HSMV-1 | Myosin of myofibroblasts |
| CT3 | Troponin T |
| Anti-troponin I | Troponin I |
| P2B1 | VCAM -endothelial cells |
| P4A4 | E-selectin |
| IA4 | Smooth muscle alpha-actin |
| CIICI | Collagen type II (cartilage) |
| MPIII | Osteopontin (bone) |
| WVIDI | Bone sialoproteins I and II |
| Ectodermal Phenotypes: | |
| Anti-Neurofilament 160 (NF-160) | Neurofilament 160 kDa |
| Anti-Neurofilament 200 (NF-200) | Neurofilament 200 kDa |
| Anti-β-III-tubulin | Neurofilament |
| RT-97 | Phosphorylated epitope on neurofilament |
| Anti-synapsin | Synapsin I protein at nerve terminals |
| Anti-CNPase (anti-2'3'cyclic nucleotide-3'phosphodiesterase) | Enzyme associated with oligodendrocytes |
| Anti-GFAP (glial fibrillary acidic protein) | Reactive astrocytes and immature astrocytes |
| Endodermal Phenotypes | |
| H4 | hepatocytes |
| OV-6 | hepatocytes |
| AFP | Alpha-fetoprotein |

Flow Cytometry:

Cells were counted and then transferred to a 5-ml tube, washed twice with PBS (5 min at 1,000 rpm), then resuspended in 100 μl (per $10^6$ cells) of PBS. Five microliters of Sandoglobin solution (1 mg ml) was then added and incubated on ice for 10 min, after which the sample was washed twice with PBS and resuspended in 100 μl (per $10^6$ cells) of PBS. Antibodies (appropriate silution per antibody) were then added and incubated for 20 min on ice, and then washed twice with PBS. When needed, a secondary antibody addition was conducted by resuspending in 100 μl (per 106 cells) of PBS and then adding 1-4 μl of secondary antibody (depending on the secondary antibody and its concentration), followed by a 20-min incubation.

The antibodies used were for the markers listed in Table 4. Antibodies were purchased from PharMingen. Antibodies were directly conjugated to various fluorochromes, Dead cells were eliminated by using the viability dye 7AAD. Flow cytometry was performed on a FACSVantage (Becton Dickinson). Side scatter and forward scatter profiles were used to eliminate cell doublets.

PCR

Total RNA was extracted using RNAzol B (Tel-Test, Inc., Friendswood, Tex.) and treated with DNase. mRNA was reverse transcribed and cDNA was amplified by real-time PCR in a LightCycler (Roche Diagnostics, Indianapolis, Ind.) using SYBRGreen Taq Readymix (Sigma-Aldrich, St Louis, Mo.). Oligonucleotide primer sequences are shown in Table 3. Positive standards were made from 10-fold serial dilutions of gel-quantified PCR products. mRNA levels were normalized using the GAPDH external standard as the housekeeping gene. All positive samples were amplified without the RT step to confirm an absence of DNA contamination.

TABLE 3

Real-time PCR of Oct4, ZFP42, Nestin, Sox1 and GAPDH

| Gene | Oligo Sequence | Accession # | Position | Anneal temp | Product size |
|---|---|---|---|---|---|
| Oct4 | 5'GCCAGAAGGGCAAGCGATC3' [SEQ ID NO 1] 5'CCCCCTGTCCCCCATTCCTA3' [SEQ ID NO 2] | NM_002701 | 920–1173 | 68° C. | 254 bp |
| ZFP42 | 5'AGATCCTAAACAGCTCGCAGAAT3' [SEQ ID NO 3] 5'GCGTACGCAAATTAAAGTCCAGA3' [SEQ ID NO 4] | AF450454 | 489–793 | 65° C. | 305 bp |
| Nestin | 5'CCTACAGAGCCAGATCGCTCAGG3' [SEQ ID NO 5] 5'GGTCCTAGGGAATTGCAGCTCC3' [SEQ ID NO 6] | NM_006617 | 952–1147 | 65° C. | 196 bp |
| Sox1 | 5'ACTTTCCTCCGCGTTGCTTC3' [SEQ ID NO 7] 5'GGTGGTGGTGGTAATCTCTTTG3' [SEQ ID NO 8] | NM_005986.2 | 1606–1782 | 65° C. | 177 bp |
| GAPDH | 5'GAAGGTGAAGGTCGGAGTC3' [SEQ ID NO 9] 5'GAAGATGGTGATGGGAATTC3' [SEQ ID NO 10] | M33197.1 | 66–291 | 65° C. | 226 bp |

Histochemical Assays:

Assays for phenotypes have been previously described[1]. Therefore, a brief synopsis is provided. Mineralized tissue was assayed by von Kossa's stain. Cartilage was assayed by Alcian blue (Roboz Surgical Instrument, Rockville, Md.). Fat was assayed by Sudan Black B (Asbey Surgical Co., Washington, D.C.). Muscle was assayed by MF-20 antibody to skeletal muscle myosin (Hybridoma Bank, Ames, Iowa). Smooth muscle was assayed with an antibody to smooth muscle α-actin kit (Sigma). Endothelial cells were assayed by their uptake of low density lipoprotein, DiI-Acyl-LDL (Biomedical Technology, Stoughton, Mass.).

RESULTS

Isolation and Self-Renewal:

Isolation of pluripotent adult stem cells (PPASCs) is a two-step process. The first step is isolation of mononuclear cells from the tissue followed by primary culture. We have obtained PPASCs from the dermis, marrow, and skeletal muscle. We routinely obtain from $0.5 \times 10^5$ to $2 \times 10^6$ mononuclear cells per ml of primary tissue. Cells have been obtained from a newborn (foreskin) to a 67 year old individual. These cells are expanded in culture and then subjected to the second step: a freeze-thaw process to isolate the PPASCs. Recovery of viable cells ranged from 24% to 100%, but was usually between 80-90%. Primary cultures derived from skeletal muscle consisted of stellate-shaped cells and bipolar cells. Bipolar cells fused to form myotubes during the primary culture (FIG. 1A). Stellate cells did not demonstrate any change in morphology. Primary cultures derived from bone marrow or skin consisted of stellate-shaped cells, spindle-shaped cells, and cells that accumulated vesicles of a clear liquid (adipocytes). Secondary cultures (post freeze/thaw) derived from both skeletal muscle and marrow consisted of stellate-shaped cells only.

The cells can be maintained in culture for multiple passages without any sign of senescence. Ability for self-renewal was examined by calculating population doublings for one of the preparations: HmSC-9, which was cultured as described in Methods and trypsinized when the cultures reached confluence The number of the cells was counted following each passage. The population doublings were calculated from the number of cells initially plated and the number present after incubation. The total number of cell doublings was 169. The number of cell doublings per passage ranged from two to 7. Both the mean and median of cell doublings per incubation were five. In the CD profile reported below, we report the results for passage 11 for preparation HmSC-9 F4P11 (P denotes the cumulative passage # while F denotes the number of times the cells were frozen-thawed) and this corresponds to 62 cell doublings. HmaSC-3 refers to a preparation from bone marrow and the F1P3 denotes that the cells have been frozen/thawed once (F1) and are in their third passage (P3).

CD Profile

The CD profile and other cell surface or protein markers of two batches of PPASCs are presented in Table 4, with one profile from PPASCs isolated from skeletal muscle (HmSC-9) and the other profile from PPASCs isolated from bone marrow (HmaSC-3). The profile from HmSC-9 and HmaSC-3 was repeated twice. PPASCs are negative for lineage markers of differentiated hematopoietic cells (lin−).

PPASCs are positive for CD13, CD34 (while proliferating), CD56, CD90, CD117 (c-kit), and nestin by immunohistochemistry.

TABLE 4

| CD | HmaSC-3 F1P3 | HmSC-9 F4P11 | CD | HmaSC-3 F1P3 | HmSC-9 F4P11 |
|---|---|---|---|---|---|
| 1a | | | 57 | | |
| 2 | neg | neg | 59 | | |
| 3 | Neg | neg | 61 | | |
| 4 | | | 62e | | |
| 5 | neg | neg | 64 | neg | neg |
| 7 | | | 65 | | |
| 8 | | | 66e | | |
| 9 | | | 68 | | |
| 10 | neg | neg | 69 | | |
| 11b | | | 71 | | |
| 11c | | | 79 | | |
| 13 | pos | pos | 83 | | |
| 14 | neg | neg | 90 | pos | pos |
| 15 | | | 105 | | |
| 16 | Neg | neg | 117 | pos | pos |
| 18 | | | 123 | | |
| 19 | neg | neg | 166 | | |
| 20 | | | Gly-A | | |
| 22 | | | DRII | neg | neg |
| 23 | | | FLT3 | | |
| 24 | | | FMC-7 | | |
| 25 | | | Annexin | | |
| 31 | neg | neg | nestin | pos | pos |
| 33 | neg | neg | MHC-1 | | |
| 34 | pos | pos | Flk1 | | |
| 36 | | | Muc18 | | |
| 38 | | | Tie/Tek | | |
| 41 | | | HLA-DR | | |
| 42b | | | β2-micro | | |
| 44 | | | stro-1 | neg | neg |
| 45 | neg | neg | | | |
| 49b | | | | | |
| 49d | | | | | |
| 49e | | | | | |
| 50 | | | | | |
| 55 | | | | | |
| 56 | pos | pos | | | |

PCR

Nestin is an intermediate filament protein that is expressed predominantly in stem and precursor cells of the central nervous system in the neural tube, but also found in retina, hair follicle, liver, and hematopoietic cells[13-16]. Sox1 plays a direct role in neural cell fate determination and differentiation[17]. Oct4 and ZFP42 (mouse Rex1 homolog) have been reported to be characteristically, though not exclusively, expressed by embryonal carcinoma and embryonic stem cells and to be generally down regulated upon differentiation of these cells. Therefore, it is thought that expression of these genes is associated with primitive stem cells[18].

Oct4 was expressed in marrow primary cultures and after freeze-thaw and in skeletal muscle primary culture and after freeze thaw at levels similar to Oct4 expression in the MCF7 cell line (positive control), and at 5 orders of magnitude less than expression of GAPDH. Nestin was similarly detected in primary culture and after freeze-thaw in PPASCs isolated from marrow and skeletal muscle. ZFP42 and Sox 1 were not expressed. Thus, PCR confirmed the immunohistochemical detection of nestin in the PPASCs and indicated that PPASCs express Oct4, which is also expressed by embryonic stem cells.

Differentiation Induced by Dexamethasone Treatment

Control cultures without dexamethasone consisted of stellate cells that did not change morphology. Experimental cultures of stellate cells incubated with differing concentrations of dexamethasone to yield cells of varying phenotype. A summary of phenotypes observed is presented in Table 5. Phenotypes were observed in PPASCs derived from skeletal muscle, foreskin, and bone marrow at the concentrations indicated.

TABLE 5

| Antibody | Control | $10^{-10}$ M dex | $10^{-9}$ M dex | $10^{-8}$ M dex | $10^{-7}$ M dex | $10^{-6}$ M dex |
|---|---|---|---|---|---|---|
| MF-20 | − | + | + | + | − | − |
| CT3 | − | − | − | + | ++ | + |
| Trop I | − | − | − | + | + | + |
| P2B1 | − | − | − | − | + | ++ |
| P4A4 | − | − | − | + | + | + |
| IL-1β | − | − | − | + | + | + |
| LDL uptake | − | − | − | + | ++ | ++ |
| Desmin | − | + | ++ | + | + | + |
| IA4 | − | − | − | + | ++ | + |
| CIICI | − | − | + | ++ | + | − |
| MPIII | − | + | + | + | + | − |
| WVIDI | − | + | + | + | + | − |
| Sudan Black B | − | − | − | + | ++ | ++ |
| CNPase | − | ++ | ++ | + | − | − |
| GFAP | − | + | ++ | − | − | − |
| Talin | − | − | + | ++ | ++ | − |
| H4 | − | − | + | + | + | − |
| OV-6 | − | − | − | − | + | + |
| AFP | − | − | + | + | ++ | + |

Legend:
− = no stained cells seen per culture well.
+ = 1–5 cells seen per culture well.
++ = 5–10 cells observed per culture well.
MF-20 = Skeletal muscle; antibody to the heavy chain of myosin
CT3 = cardiac muscle; antibody to cardiac troponin T
Trop I = cardiac muscle; antibody to cardiace troponin I
P2B1 = Endothelial cells; antibody to human umbilical vein endothelial cells.
P4A1 = endothelial cells; antibody to IL-1β activated human umbilical vein endothelial cells.
LDL = fluorescent labeled acetylated low density lipoprotein uptake for 20 min.
Desmin = myogenic precursor cells; antibody to desmin
IA4 = smooth muscle; antibody to α-smooth muscle actin
CIICI = cartilage; antibody to type II collagen
MPIII = bone; antibody to osteopontin
WVIDI = bone; antibody to bone sialoproteins I and II
CNPase = glial cells; antibody to the enzyme CNPase, a marker of mature astrocytes
GFAP = astrocytes; antibody to glial fibrillary acidic protein
Talin = fibroblasts; antibody to talin
H4 = liver; antibody to hepatocytes and heptocarcinomas
OV-6 = liver; antibody to hepatocytes
AFP = liver; antibody to α-fetoprotein Examples of cells staining positive for antibodies to skeletal muscle are presented in FIG. 1B, 2B. Positive staining for desmin is presented in FIG. 2A. Examples of cells positive for smooth muscle alpha actin are FIGS. 2C and 3B. Cells positive for both troponin T and troponin I were detected when the PPASCs were treated with dexamethasone (FIG. 2D), indicating differentiation into cardiac muscle. Thus, differentiation of the PPASCs into all three major muscle phenotypes—skeletal, smooth, and cardiac—was induced by dexamethasone.

Mesodermal phenotypes other than muscle phenotypes were also observed. When treated with $10^{-9}$ to $10^{-6}$ M dexamethasone, cells were observed that contained vesicles. As time progressed, the vesicles enlarged and merged until the cells contained one or two large vesicles. These vesicles stained with Sudan Black B, a stain for neutral lipid. Thus, the PPASCs also differentiated into adipocytes (FIG. 3A). Differentiation of endothelial cells were identified by four markers: uptake of acetylated low density lipoprotein (FIG. 4), an antibody to human umbilical vein endothelial cells, and an antibody against IL-1β activated endothelial cells (FIG. 5A, B). Induction of endothelial cells reproducibly occurred at concentration of dexamethasone of $10^{-8}$ M and above.

Multilayered nodules of cells were observed in the cultures of PPASCs after 3 weeks of treatment with dexamethasone. FIG. 5C shows a nodule positive for bone sialoproteins I and II. These nodules mineralized, demonstrated by staining with Von Kossa's (FIG. 6C). Confirmation that the mineral contained calcium was demonstrated by pretreating the cultures with EGTA to chelate the calcium, whereupon there was no staining of the nodule with Von Kossa's (FIG. 6D). Staining with antibodies to type II collage showed nodules whose extracellular matrix was positive (FIG. 5C) while sulfated proteoglycans were detected by staining with Alcian blue pH 1.0 (FIG. 6B). Therefore the PPASCs differentiated into both osteoblasts and chondrocytes.

Some areas of the culture exhibited cells that were spindle shaped and grew in swirl patterns (FIG. 6A), the morphology typical of fibroblasts. Cells positive to talin, a marker for fibroblasts, were also observed (FIG. 5E).

Dexamethasone also induced the PPASCs to differentiate to phenotypes of the ectodermal lineage. An example of positive staining for 160 kD neurofilament, a marker for neurons, is seen in FIG. 7A. FIG. 7B depicts cells stained with antibody to glial fibrillary acidic protein (GFAP), an antibody to astrocytes. Cells positive for CNPase, a marker for oligodendrocytes, was also observed with dexamethasone treatment (FIG. 7C, FIG. 8A).

We were able to detect markers for hepatocytes in PPASCs induced to differentiate with dexamethasone. Hepatocytes were detected by 3 different antibodies: H4 (FIG. 8B), OV-6 (FIG. 8C) and α-fetoprotein (FIG. 8D). The highest quantity of hepatocytes was observed with $10^{-8}$ M dexamethasone treatment.

Neural Induction of PPASCs by Neurosphere and Neurococktail

Identification of neural stem cells in vitro has been accomplished by culturing the putative neural stem cells in three-dimensional aggregates or "neurospheres" in the presence of neurotrophic factors. The cells are then dissociated as assayed for neural characteristics such as phenotypic protein markers and, in the case of neurons, the ability to respond to glutamate with an influx of calcium. More recently, putative stem cells derived from sources outside the CNS or PNS have been cultured in monolayer in the presence of neurotrophic chemicals in order to induce the cells to a neural fate.

Treatment with Neural Cocktail:

Following the neural cocktail protocol, the cells were fixed and immunostained for proteins specific for neural phenotypes. There was no evidence of neural morphology in cultures of PPASCs that did not receive the neural cocktail (FIG. 9A), nor did the cells stain for any of the neural antibodies. FIG. 8A depicts cells that did not receive neural cocktail stained with antibody to RIP, a protein specific for oligodendrocytes. FIG. 9A shows adult stem cells that did not receive the neurococktail but were stained with antibody to β-III-tubulin for neurons; there were no β-tubulin positive cells. Neurococktail treated cultures stained with antibodies to phosphorylated neurofilament (neurons), β-tubulin III (neurons), and GFAP (astrocytes) (FIGS. 9B, C, and D, respectively). It appeared that nearly all cells in the cultures were positive for one of the three neural phenotypes. Aproximately 60% of the human adult stem cells treated with the neurococktail for 48 h were positive for β-III-tubulin and had an elongated morphology with, typically, 2 processes. The morphology of the individual adult stem cells treated with the neurococktail ranged from round cells (FIG. 9B, D blue arrows) to elongated neuronal type cells with thin processes (FIG. 9B, D black arrows). However, even the cells with seemingly undifferentiated morphology had positive staining for some of the neural antibodies. In FIG. 8C, black arrow points to a cell with neuronal morphology while in FIG. 9D the black arrows denote cells positive for anti-GFAP that has shorter multiple processes. The red arrows denote cells in the background that did not stain at all for the neural antibodies applied (FIG. 9B, D).

The cultures were also tested with antibodies to muscle phenotypes (FIG. 10). The application of the neurococktail resulted in cells positive for antibodies to the muscle specific proteins desmin and sarcomeric myosin (antibody MF-20) (FIG. 10C, D). Many of these cells had multiple nuclei characteristic of skeletal muscle myotubes (FIG. 10D) represented approximately 20% of the cells in the cultures (FIG. 10C).

Human PPASCs that were treated for 10 days past the initial 5 hour neurococktail incubation also resulted in cells that were positive for neural and muscle specific markers (FIG. 11). The neurococktail treated adult stem cells were positive for the antibody to MF20 (sarcomeric myosin) and the antibody to HSMV (myosin) (FIGS. 11A and B, respectively). These cells had a morphology that was elongated with multiple nuclei. This represents a second means of inducing muscle phenotypes and a confirmation of the ability of PPASCs to differentiate to those mesodermal phenotypes.

Cultures treated with the neurococktail for 10 days had neuronal morphologies with cells positive for antibodies to anti-NF200 and anti-β-III-tubulin neuronal proteins (FIG. 11C, D, respectively). These cells were elongated but only had one nucleus. The vast majority of cells were positive for anti-β-III-tubulin (FIG. 11D). In addition, a few cells positive for synapsin, a synaptic protein, were detected (FIG. 11E). Those proteins appeared to be clustered in blebs.

Glutamate Sensitivity/Calcium Uptake:

Neuronal cells have the ability to take up calcium in the presence of glutamate, the brain's main excitatory neurotransmitter[19] (FIG. 12A-F). PPASCs not treated and treated with neurococktail were tested for their ability to take up calcium in the presence of glutamate by observing the fluorescence of Calcium Green, which fluoresces when it binds calcium. PPASCs 10 d post treatment with neurococktail were primed with Calcium Green, washed to remove excess Calcium Green, and then incubated in media with 60 mM glutamate. Cultures not treated with neurococktail had no fluorescence (data not shown). PPASCs treated with neurococktail had no fluorescence at 0 minutes after the addition of glutamate (FIG. 12A). Fluoresence rapidly increased between 0 and 10 minutes (FIG. 12B, C) and then remained relatively constant up until 60 minutes (FIG. 12C, D, E). A light microscope picture of the cells is shown in FIG. 12F. The fluorescence was primarily localized to the cell body of the neurococktail treated adult stem cells.

Neurosphere Protocol:

The neurosphere protocol is the most common means of inducing neural differentiation of tem cells. Human adult stem cells isolated from skeletal muscle and cultured by the neurosphere protocol exhibited small clusters of approximately 3-20 cells on day 3 of suspension culture (FIG. 13A). These clusters had either clumped or the cells in the culture had proliferated to form larger clusters or spheres of approximately 100-200 cells by day 11 (FIG. 13B). The neurospheres were dissociated on day 14 and the cells replated in attachment culture, which is reported to be necessary for differentiation.[5] At the initiation of attachment culture, the neural differentiating factor, NT-3, was added to the media and EGF and FGF removed. Following the 3 days of attachment culture (day 17 since initiation of the neurosphere protocol), the cultures consisted of solitary attached cells with a few small attached spheres (FIG. 13C). At day 22 of the protocol (8 days of attached culture), the cultures consisted of cells in long interconnected cords (denoted by the black arrows, FIG. 13D).

Neurosphere protocol treated human PPASCs were positive for markers to all three of the neural lineages, seen both in single cells and partially dissociated spheres (FIGS. 14-16). A low magnification view of the cultures show many attached cells positive for CNPase, a marker for oligodendrocytes, and a few CNPase-positive attached neurospheres. The single attached cells tend to be present in clusters. Higher magnification of one such cluster in phase contrast microscopy (FIG. 14A) and fluorescent microscopy (FIG. 14B) shows a few intensely CNPase-positive cells among less intensely stained cells. FIGS. 14C (phase contrast) and 14D (fluorescent microscopy) show larger cords of cells. These cords contain intensely positive cells (arrows) among less intensely stained cells, similar to what is seen in the smaller clusters. The partially dissociated neurosphere shown in phase contrast in FIG. 14E is intensely positive for CNPase (FIG. 14F). The cells outside of the partially dissociated sphere are elongated and appear to be neuronal in morphology but are also slightly positive for CNPase (FIG. 14G, H). Another neurosphere (FIG. 14H) shows an intensely stained sphere but the cells emerging from the sphere are only slightly positive for CNPase.

Neurosphere protocol treated human adult stem cells were also positive for antibodies to neurofilament (FIG. 15). Cells positive for anti-β-tubulin-III were observed in a partially dissociated attached neurosphere (FIG. 15A, B). As with staining for CNPase, the attached neurosphere appears as though all the cells in the sphere are β-tubulin III positive, but this is probably an artifact of the three dimensional structure. Individual attached cells with elongated processes positive for β-tubulin were also seen (FIGS. 15C and D). Cells positive for neurofilaments of 160 kDa (NF-160) were also observed. These cells were observed in both attached neurospheres and in isolated attached cells (FIGS. 15E and F). The box depicts a cell in the culture that was not positive for the NF-160 antibody for neurons (FIG. 15E, F). Although the majority of the neurosphere protocol treated human adult stem cells were positive for markers for either oligodendrocytes or neurons, a few cells were positive for GFAP, a marker for astrocytes (FIG. 15G, H). Unlike the staining for CNPase, β-tubulin III, and the 160 kD neurofilament, the entire attached neurosphere is not intensely positive. The sphere is diffusely positive with several clearly discernible positive cells (FIG. 15G, H). However, the number of GFAP positive cells seems to be very low compared with the total number of cells in the neurosphere (FIG. 15G, H). Morphologically, these cells do not possess any neural extensions and appear more rounded than the cells positive for neuronal and oligodendrocyte markers.

As in the attached adult stem cells treated with neurococktail, cultures treated with the neurosphere protocol also had cells positive for desmin (FIG. 16). These cells were not in the attached neurospheres but were present in the attached individual cells. The desmin positive cells were not as elongated as the β-tubulin III or 160 kD neurofilament positive cells but were instead more irregularly shaped without thin extending processes. Thus there is a third way in which muscle phenotypes can be induced in the PPASCs.

REFERENCES

1. Lucas, P. A., Calcutt, A. F., Southerland, S. S., Wilson, A., Harvey, R. Warejcka, D., and Young, H. E. A population of cells resident within embryonic and newborn rat skeletal muscle is capable of differentiating into multiple mesodermal phenotypes. *Wound Repair and Regeneration*, 3: 449-460, 1995.
2. Woodbury D, Reynolds K & Black I B. Adult bone marrow stromal stem cells express germline, ectodermal, endodermal, and mesodermal genes prior to neurogenesis. The Journal of Neuroscience 69(6), 908-917. 2002.
3. Romero-Ramos M et al. Neuronal differentiation of stem cells isolated from adult muscle. Journal of Neuroscience Research 69, 894-907. 2002.
4. Woodbury D, Schwarz E J, Prockop D J & Black I B. Adult rat and human bone marrow stromal cells differentiate into neurons. Journal of Neuroscience Research 61, 364-370. 2000.
5. Reynolds B A & Weiss S. Generation of neurons and astrocytes from isolated cells of the adult mammalian central nervous system. Science 255(5052), 1707-1710. 1992.
6. Wachs F et al. High efficacy of clonal growth and expansion of adult neural stem cells. Laboratory Investigation 83(7), 949-962. 2003.
7. Woodbury D, Schwarz E J, Prockop D J & Black I B. Adult rat and human bone marrow stromal cells differentiate into neurons. Journal of Neuroscience Research 61, 364-370. 2000.
8. Nunes M C et al. Identification and isolation of multipotential neural progenitor cells from the subcortical white matter of the adult human brain. Nature Medicine 9(4), 439-447. 2003.
9. McDonald J W et al. Transplanted embryonic stem cells survive, differentiate, and promote recovery in injured rat spinal cord. Nature Medicine 5(12), 1410-1412. 1999.
10. Hanson M G Jr, Shen S, Wiemelt A P, McMorris F A & Barres B A. Cyclic AMP elevation is sufficient to promote the survival of spinal motor neurons in vitro. The Journal of Neuroscience 18(18), 7361-7371. 1998.
11. Roy N S et al. In vitro neurogenesis by progenitor cells isolated from the adult human hippocampus. Nature Medicine 6(3), 271-277. 2000.
12. Pincus D W et al. Fibroblast growth factor-2/brain-derived neurotrophic factor-associated maturation of new neurons generated from adult human subependymal cells. Annals of Neurology 43(5), 576-585. 1998.
13. Li L, Mignone J, Yang M, Matic M, Penman S, Enikolopov G, Hoffman, Nestin expression in hair follicle sheath progenitor cells Proc Natl Acad Sci U S A. 2003 August 19;100(17):9958-61
14. Mayer E J, Hughes E H, Carter D A, Dick A D. Nestin positive cells in adult human retina and in epiretinal membranes. Br J Ophthalmol. 2003 September;87(9):1154-8
15. Sun X Y, An J. Expression of nestin, an intermediate filament protein, in human fetal hepatic stem cells. Di Yi Jun Yi Da Xue Xue Bao. 2004 February;24(2):207-9.

16. Ha Y, Lee J E, Kim K N, Cho Y E, Yoon D H. Intermediate filament nestin expressions in human cord blood monocytes (HCMNCs). Acta Neurochir (Wien). 2003 June; 145(6):483-7.
17. Kan L, Israsena N. Zhang Z, Hu M, Zhao L R, Jalali A, Salni V, Kessler J A. Sox1 acts through multiple independent pathways to promote neurogenesis. Dev Biol. 2004 May 15;269(2):580-94.
18. Henderson J K, Draper J S, Baillie H S, Fishel S, Thomson J A, Moore H, Andrews P W. Preimplantation human embryos and embryonic stem cells show comparable expression of stage-specific embryonic antigens. Stem Cells. 2002;20(4):329-37.
19. Holden C. Neuroscience. White matter's the matter. 299 (5905), 334. 2003.

What is claimed is:

1. Isolated human pluripotent adult stem cells which express CD13, CD34, CD56 and CD117, and which do not express CD10.

2. The isolated human pluripotent adult stem cells of claim 1, which further do not express CD2, CD5, CD14, CD19, CD33, CD45, and DRII.

3. The isolated human pluripotent stem cells of claim 1, which express CD13,CD34, CD56, CD90, CD117 and nestin, and which do not express CD2, CD3, CD10, CD14, CD16, CD31, CD33, CD45and CD64.

4. The isolated human pluripotent adult stem cells of claim 1, isolated from a human skeletal muscle.

5. The isolated human pluripotent adult stem cells of claim 1, isolated from a human bone marrow.

6. The isolated human pluripotent adult stem cells of claim 2, isolated from a human skeletal muscle.

7. The isolated human pluripotent adult stem cells of claim 2, isolated from a human bone marrow.

8. The isolated human pluripotent adult stem cells of claim 3, isolated from a human skeletal muscle.

9. The isolated human pluripotent adult stem cells of claim 3, isolated from a human bone marrow.

10. A composition comprising the isolated human pluripotent adult stem cells of claim 1.

11. A composition comprising the isolated human pluripotent adult stem cells of claim 2.

12. A composition comprising the isolated human pluripotent adult stem cells of claim 3.

13. A biodegradable matrix comprising the isolated human pluripotent adult stem cells of claim 1.

14. A biodegradable matrix comprising the isolated human pluripotent adult stem cells of claim 2.

15. A biodegradable matrix comprising the isolated human pluripotent adult stem cells of claim 3.

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: Artificial
<220> FEATURE:
<223> OTHER INFORMATION: Chemically synthesized

<400> SEQUENCE: 1
gccagaaggg caagcgatc                                                    19

<210> SEQ ID NO 2
<211> LENGTH: 20
<212> TYPE: DNA
<213> ORGANISM: Artificial
<220> FEATURE:
<223> OTHER INFORMATION: Chemically synthesized

<400> SEQUENCE: 2 cccctgtcc cccattccta                                                    20

<210> SEQ ID NO 3
<211> LENGTH: 23
<212> TYPE: DNA
<213> ORGANISM: Artificial
<220> FEATURE:
<223> OTHER INFORMATION: Chemically synthesized

<400> SEQUENCE: 3
agatcctaaa cagctcgcag aat                                               23

<210> SEQ ID NO 4
<211> LENGTH: 23
<212> TYPE: DNA
<213> ORGANISM: Artificial
<220> FEATURE:
<223> OTHER INFORMATION: Chemically synthesized

<400> SEQUENCE: 4
gcgtacgcaa attaaagtcc aga                                               23

<210> SEQ ID NO 5
<211> LENGTH: 23
<212> TYPE: DNA
<213> ORGANISM: Artificial
<220> FEATURE:
<223> OTHER INFORMATION: Chemically synthesized

<400> SEQUENCE: 5
cctacagagc cagatcgctc agg                                               23

<210> SEQ ID NO 6
<211> LENGTH: 22
<212> TYPE: DNA

-continued

```
<213> ORGANISM: Artificial
<220> FEATURE:
<223> OTHER INFORMATION: Chemically synthesized

<400> SEQUENCE: 6
ggtcctaggg aattgcagct cc                                              22

<210> SEQ ID NO 7
<211> LENGTH: 20
<212> TYPE: DNA
<213> ORGANISM: Artificial
<220> FEATURE:
<223> OTHER INFORMATION: Chemically synthesized

<400> SEQUENCE: 7
actttcctcc gcgttgcttc                                                 20

<210> SEQ ID NO 8
<211> LENGTH: 22
<212> TYPE: DNA
<213> ORGANISM: Artificial
<220> FEATURE:
<223> OTHER INFORMATION: Artificial

<400> SEQUENCE: 8
ggtggtggtg gtaatctctt tg                                              22

<210> SEQ ID NO 9
<211> LENGTH: 19
<212> TYPE: DNA
<213> ORGANISM: Artificial
<220> FEATURE:
<223> OTHER INFORMATION: Chemically synthesized

<400> SEQUENCE: 9
gaaggtgaag gtcggagtc                                                  19

<210> SEQ ID NO 10
<211> LENGTH: 20
<212> TYPE: DNA
<213> ORGANISM: Artificial
<220> FEATURE:
<223> OTHER INFORMATION: Chemically synthesized

<400> SEQUENCE: 10
gaagatggtg atgggaattc                                                 20
```